(12) United States Patent
Mondal et al.

(10) Patent No.: US 10,100,079 B2
(45) Date of Patent: Oct. 16, 2018

(54) PROGESTERONE-CATIONIC LIPID HYBRID AS ANTICANCER AGENT AND THE PROCESS OF SYNTHESIS THEREOF

(71) Applicant: Council of Scientific & Industrial Research, New Delhi (IN)

(72) Inventors: Sujan Kumar Mondal, Hyderabad (IN); Sudhakar Jinka, Hyderabad (IN); Rajkumar Banerjee, Hederabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/649,832

(22) Filed: Jul. 14, 2017

(65) Prior Publication Data
US 2018/0194798 A1 Jul. 12, 2018

(30) Foreign Application Priority Data
Jul. 28, 2016 (IN) .............................. 201611025818

(51) Int. Cl.
*C07J 41/00* (2006.01)
*A61P 35/00* (2006.01)

(52) U.S. Cl.
CPC ............. *C07J 41/005* (2013.01); *A61P 35/00* (2018.01); *C07J 41/0033* (2013.01)

(58) Field of Classification Search
None
See application file for complete search history.

(56) References Cited

U.S. PATENT DOCUMENTS 7,700,559 B2 * 4/2010 Millar .................... A61K 47/64
424/1.45

* cited by examiner

*Primary Examiner* — Samantha L Shterengarts
(74) *Attorney, Agent, or Firm* — Dinsmore & Shohl LLP

(57) ABSTRACT

The present invention relates to the development of the cationic progesterone compounds as a novel anti-tumor agent. The present invention provides a method for the preparation of novel series of progesterone derivatives. The invention also provides information related to highly selective anti-cancer activities of these compounds in wide range of cancer cell irrespective of their progesterone receptor status. Thus, the presently disclosed cationic progesterone compounds offer a viable option as anti-cancer therapeutics.

9 Claims, 13 Drawing Sheets

PROGESTERONE-CATIONIC LIPID HYBRID AS ANTICANCER AGENT AND THE PROCESS OF SYNTHESIS THEREOF

CROSS-REFERENCE TO RELATED APPLICATIONS

This application claims priority to Indian Application No. 201611025818 entitled "PROGESTERONE-CATIONIC LIPID HYBRID AS ANTICANCER AGENT AND THE PROCESS OF SYNTHESIS THEREOF," filed Jul. 28, 2016, which is hereby incorporated in its entirety by reference.

FIELD OF THE INVENTION

The present invention relates to novel series of cationic lipid modified progesterone derivatives towards treating tumor. Particularly, the present invention relates to novel cationic lipid modified progesterone derivatives of general formula 6.

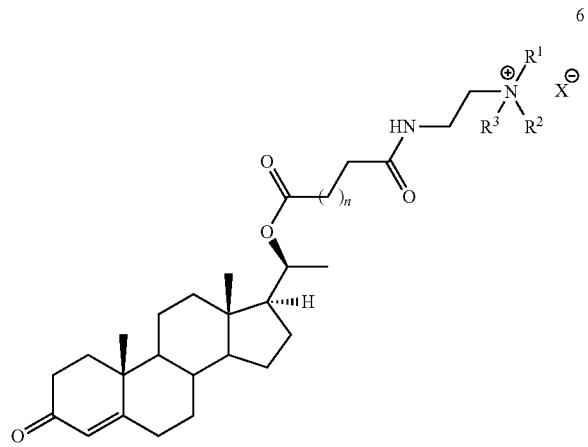

6 wherein: each of $R^1$ and $R^2$ is independently hydrogen or a lipophilic moiety containing a saturated alkyl chain, or a mono-, di- or tri-unsaturated alkenyl chain, each containing from 6 to 22 carbons, provided both $R^1$ and $R^2$ are not hydrogen; $R^3$ is independently a $C_1$-$C_5$ straight or branched chain alkyl group; n is an integer from 1 to 2; and X is selected from chlorine, bromine and iodine atom.

The present invention further relates to a method for the preparation of novel series of cationic lipid modified progesterone derivatives of general formula 6. The invention provides information about highly selective anticancer activities of these molecules in wide range of cancer cell lines. The area of medical science that is likely to benefit most from the present invention is chemotherapy against cancer.

BACKGROUND OF THE INVENTION

Sex steroid hormones such as progestin, oestrogen are involved in the growth and development of reproductive system and secondary sex characteristics. Growing evidences suggests that these hormones also play critical roles in the development and progression of tumors of the prostate, ovary, breast, liver, endometrial and skin (Lens, M. et al. Cancer Causes Control. 2008, 19, 437-442; Driscoll, M. S. et al. J. Am. Acad. Dermatol. 2007, 57, 919-931;). For example, the role of estrogen in the development and growth of breast cancer is well established and based on that, drugs against breast cancer have been developed which target Estrogen Receptor (ER) (Freedman, R. A. et al. Breast. 2010, 19, 69-75;). However, the role of progestins in breast cancer remains contradictory as some reports suggest that progestins such as Medroxyprogesterone acetate (MPA) and megestrol acetate may be used against breast cancer (Hultborn, R. et al. Wallgren, Acta. Oncol. 1996, 35, 75;), while other reports showed antiprogestins as an effective treatment option for breast cancer (Edwards, D. P. et al. J. Steroid Biochem. Mol. Biol. 1995, 53, 449-458;). Moreover, it is also demonstrated that both progesterone and antiprogesterone (mifepristone) can exert anti-proliferative effect on non-reproductive tissues regardless of progesterone receptor (PgR) expression status (Ivarsson, K. et al. Gynecol Oncol. 2001, 82, 116-121;). Given the conflicting role of progesterone and antiprogestins in cancer, it is challenging to develop progesterone-based modified therapeutics that work against both PgR-positive and PgR-negative cancer but at the same time remain non-toxic towards healthy cells.

Recently it has been demonstrated that progestin like MPA (progesterone modified molecule), a potential candidate for breast cancer therapeutics, but often fail to exert its anticancer activity due to persistent activity of the PI3K/AKT [phos-phatidylinositol 3-kinase (PI3K)] survival pathway (Riggio, M. et al. Carcinogenesis. 2012, 33, 509-518;). PI3K/AKT pathway, a key regulator in the event of cell proliferation, cell cycle, survival, apoptosis, migration and angiogenesis is frequently altered in many cancers (Kao, G. D. et al. J. Biol. Chem. 2007, 282, 21206-21212;). The activation of AKT by PI3K resulted in the activation of Mdm2, which ubiquitinylate p53, a key tumor suppressor protein, for proteasomal degradation (Surget, S. et al. Onco. Targets. Ther. 2013, 7, 57-68;). Hence, the stability or status of p53 expression in cancer cells is a well-known marker to adjudge the effect of anticancer therapeutics.

Angiogenesis plays a critical role in the formation of new blood vessels from pre-existing blood vessel (Potente, M. et al. Cell. 2011, 146, 873-887). Apart from its fundamental role in normal physiological functions like embryonic development, wound healing, reproduction, etc., it also contributes heavily in tumor growth, and metastasis. Earlier experiments demonstrated anti-angiogenic effect of MPA, (Abulafia, O. et al. Gynecol. Oncol. 1999, 72, 193-198; Ashino-Fuse, H. Int. J. Cancer. 1989, 44, 859-864). Indicating that properly functionalized progesterone or its derivatives may lead to the development of new anti-angiogenic molecules.

To date, no literature has been reported regarding the use of cationic progesterone molecule as a potent anticancer therapeutics. However, there are some reports which demonstrate the anticancer property of progesterone (Leo, J. C. et al. Int. J. Cancer. 2005, 117, 561-568;) and by its metabolites (Weibe, J. P. et al. Breast Cancer Res. 2013, 15, R38). Progesterone has also been used in anticancer treatment along with other anticancer drug such as calcitriol (Lee, L. R. et al. Cancer Prev Res. 2013, 6, 731-743), Tamoxifen (Lee, J. Y. et al. Oncol Rep. 2012, 27, 87-93; Gaston, K. et al. Patent No. WO2001082910 A2, 8 Nov. 2001) and Estrogen products (Rodriguez, G. C. U.S. Pat. No. 6,977,250 B2, 20 Dec. 2005)

SUMMARY OF THE INVENTION

The present invention provides cationic lipid modified progesterone derivatives with general formula 6,

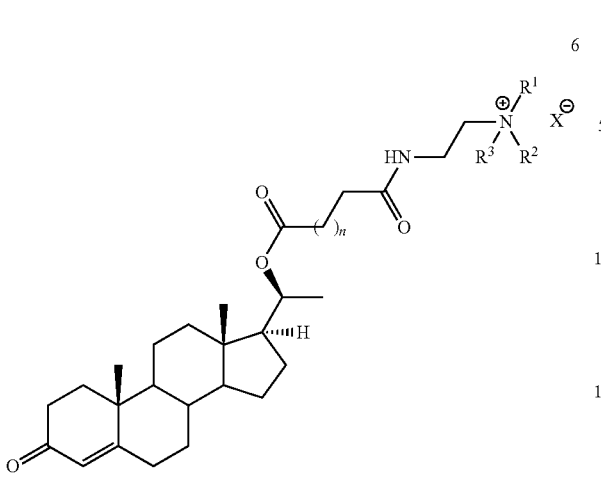

wherein: each of $R^1$ and $R^2$ is independently hydrogen or a lipophilic moiety containing a saturated alkyl chain, or a mono-, di- or tri-unsaturated alkenyl chain, each containing from 6 to 22 carbons, provided both $R^1$ and $R^2$ are not hydrogen; $R^3$ is independently a $C_1$-$C_5$ straight or branched chain alkyl group; n is an integer from 1 to 2; and X is selected from chlorine, bromine and iodine atom.

In an embodiment of the present invention, each of $R^1$ and $R^2$ is independently hydrogen or an aliphatic hydrocarbon chain provided both $R^1$ and $R^2$ are not hydrogen.

In another embodiment of the present invention, both $R^1$ and $R^2$ are aliphatic hydrocarbon chains.

In still another embodiment of the present invention, $R^3$ is C1-C5, straight or branched chain alkyl group or hydrogen atom when $R^1$ and $R^2$ are independently hydrogen or an aliphatic hydrocarbon chains provided both $R^1$ and $R^2$ are not hydrogen.

In yet another embodiment of the present invention, $R^3$ is an alkyl group and both $R^1$ and $R^2$ are aliphatic hydrocarbon chains.

In yet another embodiment of the present invention, $R^3$ is a hydrogen atom and both $R^1$ and $R^2$ are aliphatic hydrocarbon chains.

In yet another embodiment of the present invention, the representative compounds of general formula 6 are as follows:

(i) N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-hexyl-N-methylhexan-1-aminium chloride, 6a:

(ii) N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-methyl-N-octyloctan-1-aminium chloride, 6b (iii) N-decyl-N-(2-(4-((1S)-1-((10R,13S,17S)-10,13-dimethyl-3-oxo-2,3,6,7,8,9,10,11,12,13,14, 15,16,17-tetradecahydro-1H-cyclopenta[a]phenanthren-17-yl)ethoxy)-4-oxobutanamido)ethyl)-N-methyldecan-1-aminium chloride 6c.

(iv) N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-dodecyl-N-methyldodecan-1-aminium chloride 6d.

(v) N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-methyl-N-tetradecyltetradecan-1-aminium chloride 6e.

(vi) N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-hexadecyl-N-methylhexadecan-1-aminium chloride 6f.

(vii) N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-methyl-N-octadecyloctadecan-1-aminium chloride 6g.

Another embodiment of the present invention is wherein the compounds produce cytotoxic effect towards cancer cells but not in the non-cancer cell.

Yet another embodiment in the invention, compounds exhibited toxicity in cancer cell when the cationic lipid covalently conjugated with progesterone but did not exhibit any toxicity when cationic lipid added in a mixture along with progesterone.

Further embodiment of the present invention is wherein the compound arrests the cancer cell in the G2/M phase of the cell cycle.

One more embodiment of the present invention is wherein the compound showed enhanced apoptotic effect towards cancer cell.

One more embodiment of the present invention is wherein the compound showed inhibition PI3K/AKT cell survival pathway and subsequent p53 up-regulation.

Still another embodiment of the present invention is wherein the compound inhibits 75% tumor growth at a dose of 15 mg/kg of mice.

The present invention also exhibits the antiangiogenic effect of the compound.

The present invention also provides a process for the synthesis of a cationic progesterone compound of formula 6,

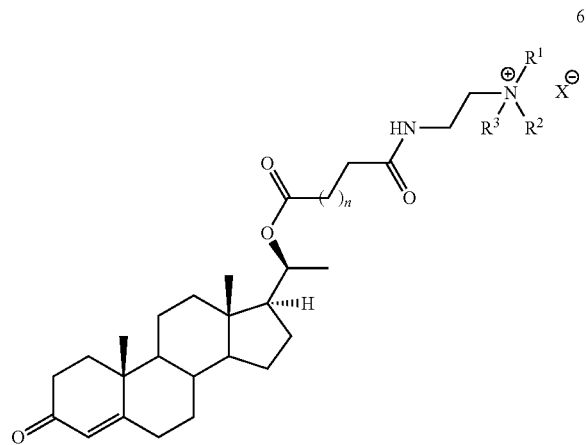

wherein: each of $R^1$ and $R^2$ is independently hydrogen or a lipophilic moiety containing a saturated alkyl chain, or a mono-, di- or tri-unsaturated alkenyl chain, each containing from 6 to 22 carbons, provided both $R^1$ and $R^2$ are not hydrogen; $R^3$ is independently a $C_1$-$C_5$ straight or branched chain alkyl group; n is an integer from 1 to 2; and X is selected from chlorine, bromine and iodine atom, wherein the process steps comprising:

(a) reducing progesterone with lithium aluminium hydride followed by regioselective oxidation by Manganese dioxide to get diastereoselective secondary alcohol intermediate with general formula 3, (b) introducing spacer (n=1 to 2) using cyclic anhydride followed by coupling with $N^1,N^1$-di- or mono-alkylethane-1,2-diamine in the presence of coupling agent EDCI in a solvent to obtain tertiary amine intermediate compound of general formula 5, (c) reacting tertiary amine compound obtained in step (b) using alkyl halide in organic solvent followed by ion exchange chromatography using halide ion exchange resins to obtain the desired quaternized compound with general formula 6.

In an embodiment of the invention wherein the cyclic anhydride used is selected from a group of succinic and glutaric anhydride consisting of 4-5 carbon atoms.

In another embodiment of the invention wherein the $N^1,N^1$-di- or mono-alkylethane-1,2-diamine used is selected from a group consisting of saturated C2-C22 alkyl groups and/or unsaturated C2-C22 alkenyl groups containing 1, 2, or 3 double bonds In yet another embodiment of the invention wherein the solvent used is selected from a group consisting of DCM, dimethyl formamide and 1,4 dioxane.

The compounds of the present invention may be used for pharmaceutical composition for the treatment of cancer comprising an effective amount of the compound of formula as claimed in claim 1 individually or in combination thereof, optionally, along with the pharmaceutically acceptable excipients, diluents.

BRIEF DESCRIPTION OF THE DRAWINGS

Scheme 1: Schematic representation of the general synthetic procedures used for the preparation of progesterone derivatives of general formula 6.

Scheme 2: Schematic representation of the synthetic route used for the preparation of 6c.

Table 1: IC50 (μM) values of Progesterone (compound 1) and its derivatives (6a-6g) in different cancer and non-cancer cell line.

Figure 1A:
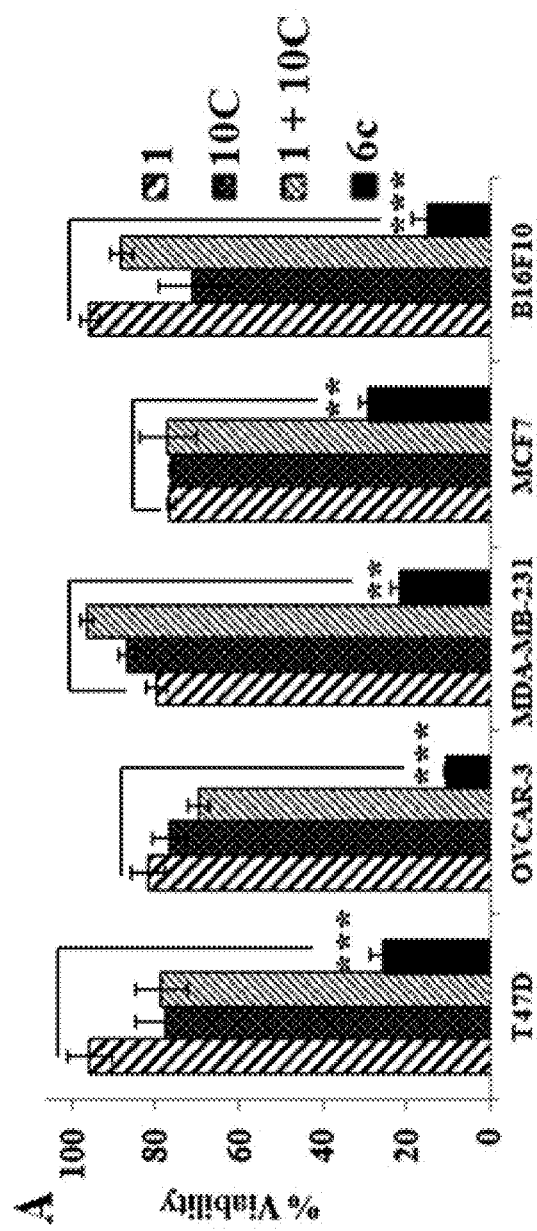

FIG. 1A: The viability studies of cancer cells T47D, OVCAR-3, MDA-MB-231, MCF-7 and B16F10 after 48 h of continuous treatment with compound 1 (10 μM), 10C [cationic lipid control molecule not containing progesterone moiety] (10 μM) 1+10C (10 μM+10 μM), 6c (10 μM).  denotes $p<0.01$; * $p<0.001$ while comparing with corresponding concentrations of Progesterone.

Figure 1B:
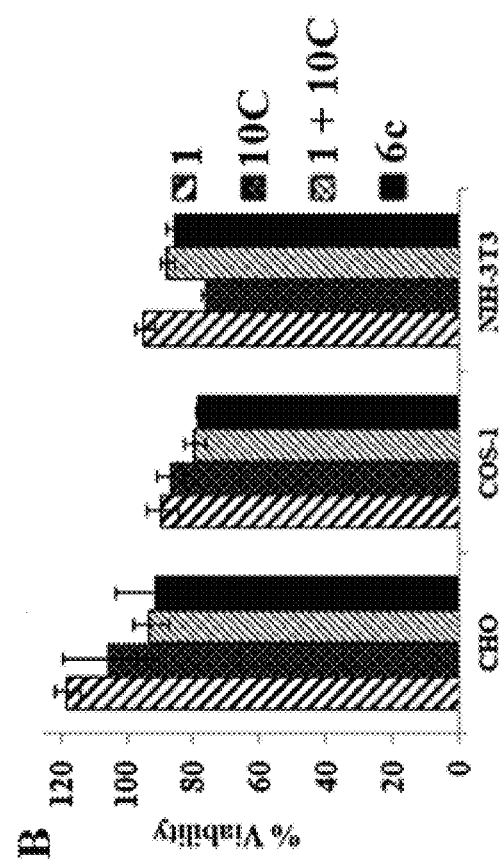

FIG. 1B: The viability studies of non-cancer cells CHO, COS-1 and NIIH-3T3 after 48 h of continuous treatment with compound 1 (10 μM), 10C [cationic lipid control molecule not containing progesterone moiety] (10 μM) 1+10C (10 μM+10 μM), 6c (10 μM).  denotes $p<0.01$; * $p<0.001$ while comparing with corresponding concentrations of Progesterone.

Figure 2A:
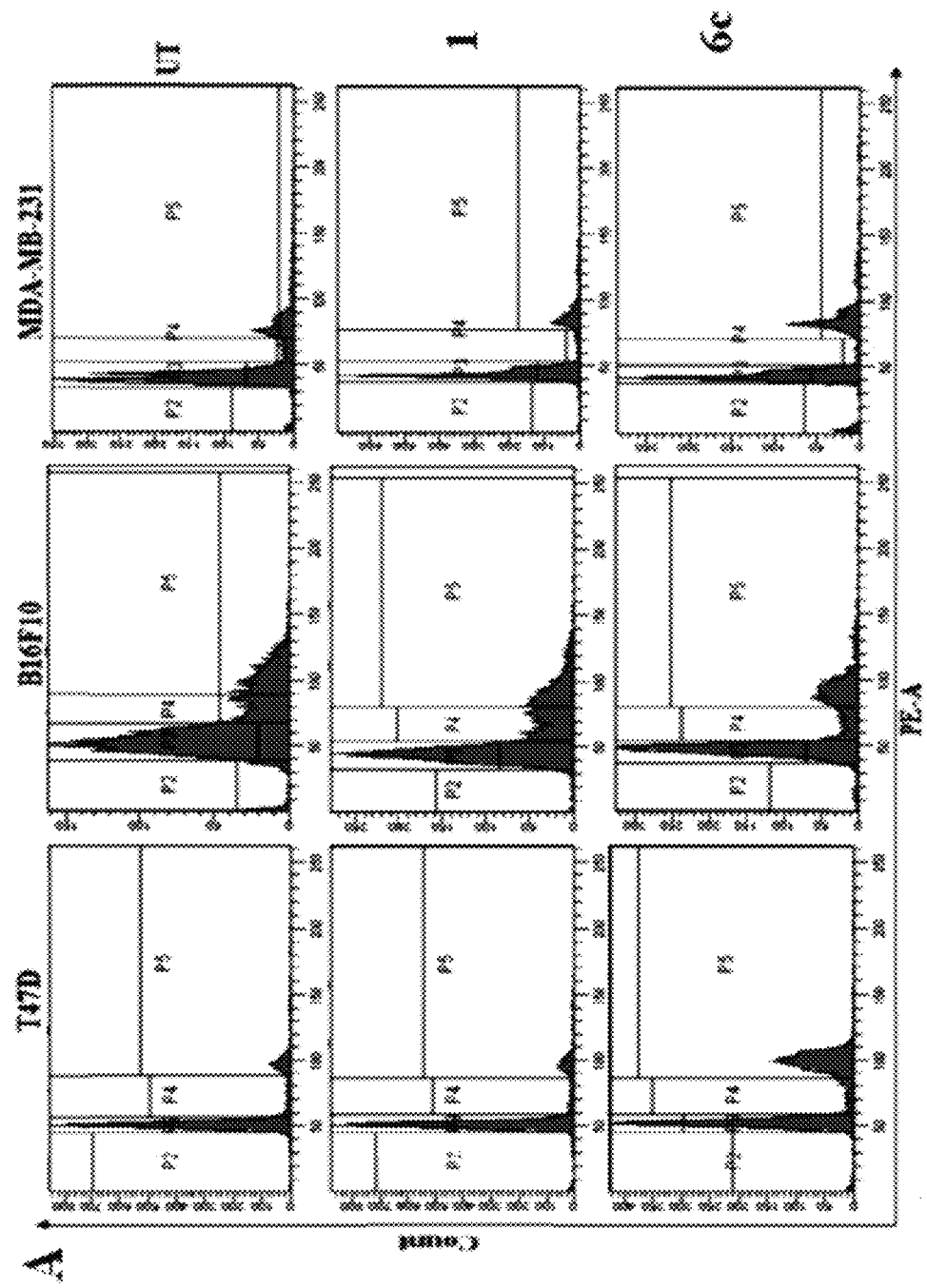

FIG. 2A: Flow cytometric analysis of cell cycle in T47D (left panels), B16F10 cells (middle panels) and MDA-MB-231 (right panel) following stained with PI. Cells were kept untreated (UT, upper panel) or treated with 10 μM of compound 1 (middle panel) or 10 μM of 6c (lower panel) for 24 h.

Figure 2B:
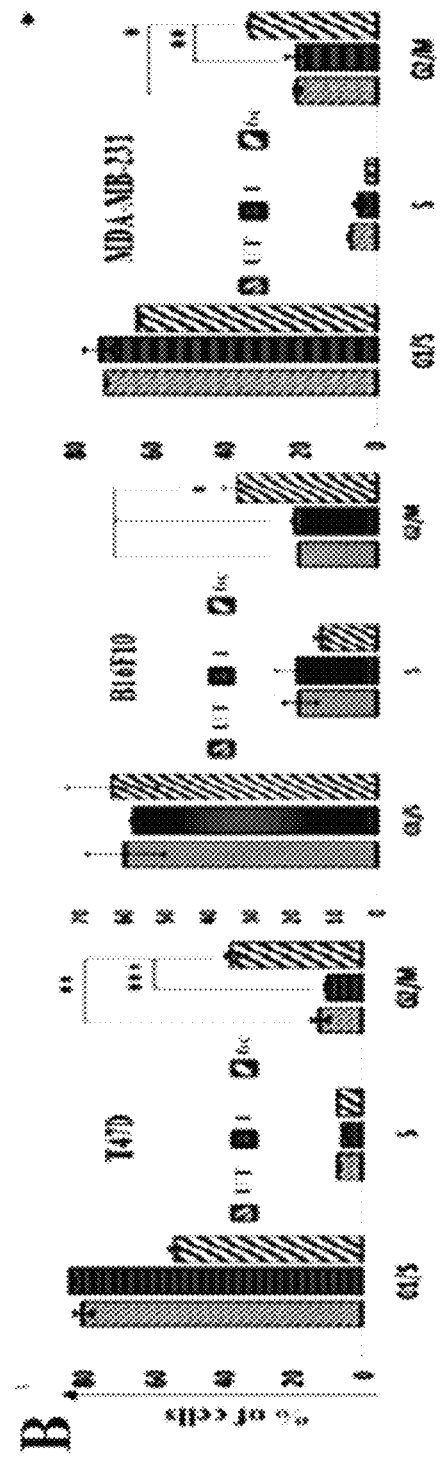

FIG. 2B: Flow cytometric analysis of cell cycle in T47D (left panels), B16F10 cells (middle panels) and MDA-MB-231 (right panel) following stained with PI. Quantitative presentation of the cell population present in different phase of the cell cycle. * denotes $p<0.05$;  denotes $p<0.01$; * $p<0.001$ while comparing either with untreated or with Progesterone.

Figure 3:
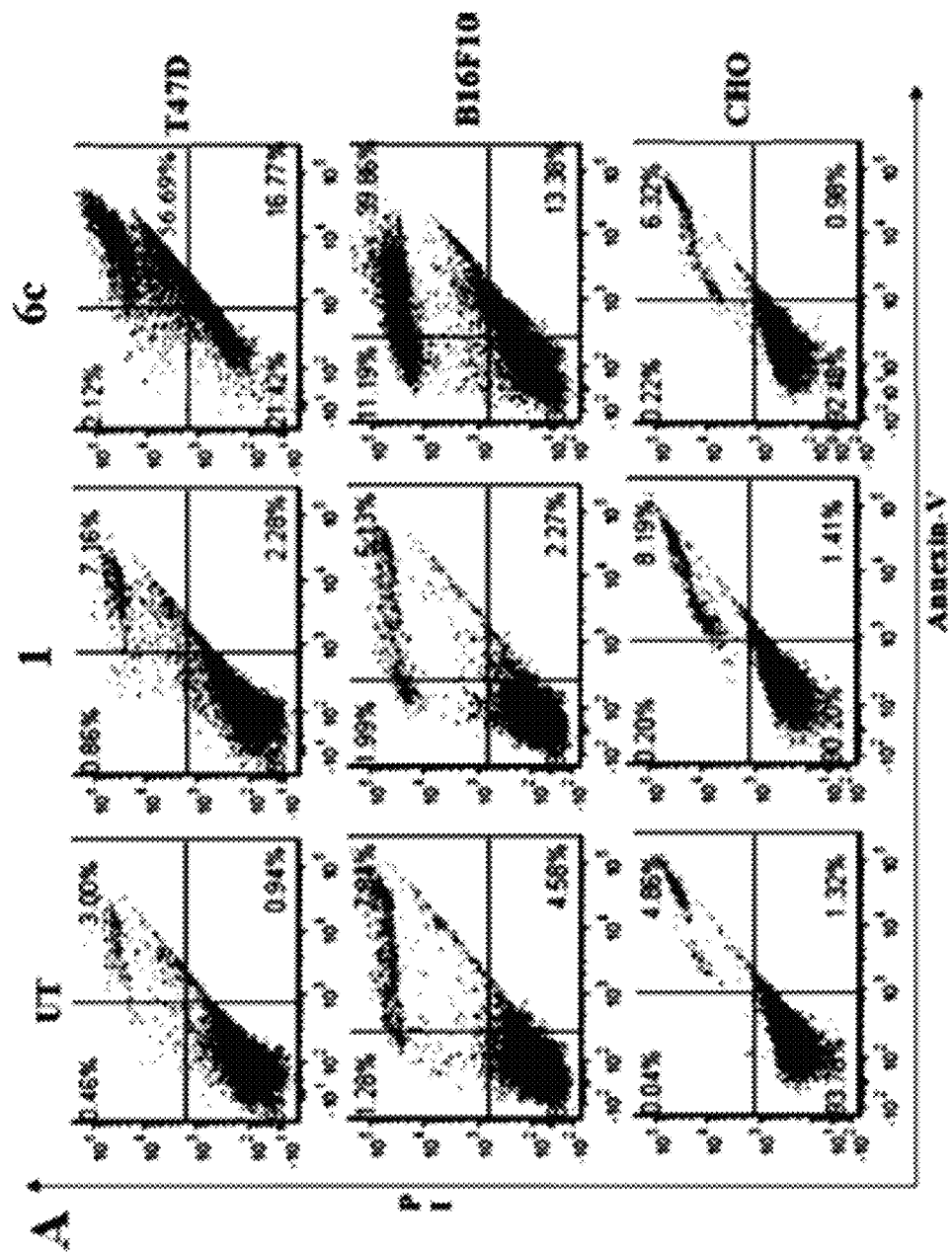

FIG. 3: (A) Apoptosis analysis by FACS in T47D, B16F10 and CHO after cells were either kept untreated (UT) or treated with compound 1 (10 μM) and 6c (10 μM) for 36 h.

Figure 4A:
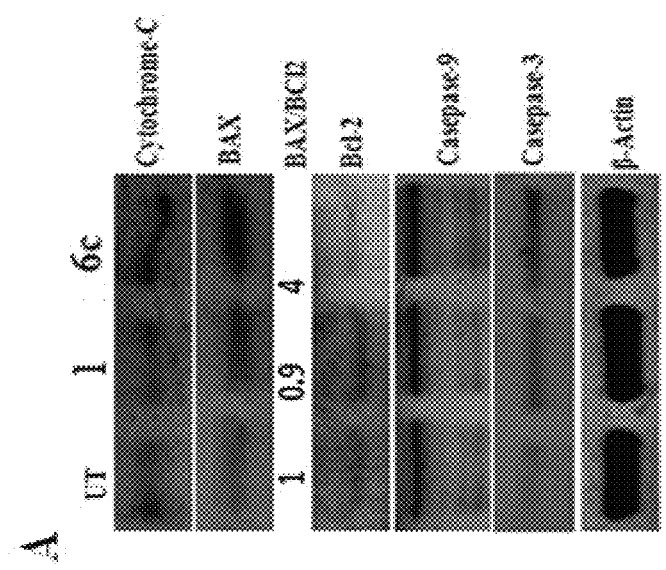

FIG. 4A: Western blot study of cellular lysates obtained from B16F10 cells after 36 h of treatment: Differential expression of apoptosis related protein.

Figure 4B:
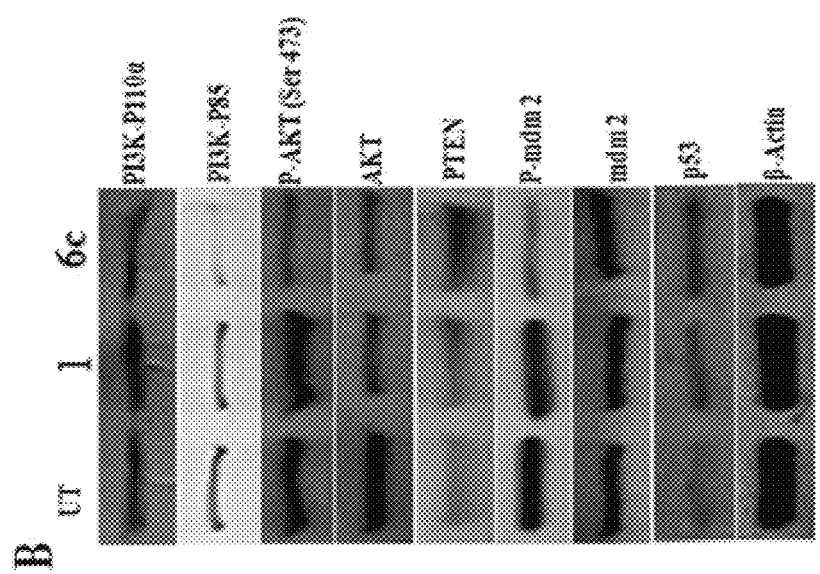

FIG. 4B: Western blot study of cellular lysates obtained from B16F10 cells after 36 h of treatment: Differential expression of PI3K/AKT pathway involving protein.

Figure 5A:
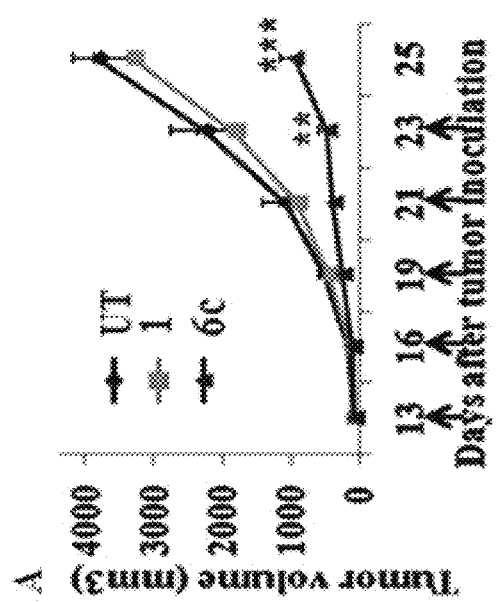

FIG. 5A: Tumor regression curve in melanoma model after 5 i.p. injection with 5% glucose (UT), compound 1 (6 mg/Kg, equivalent amount to 6c) and 6c (15 mg/Kg). Total 5 injections were given and the days of injections were indicated by black arrow.

Figure 5B:
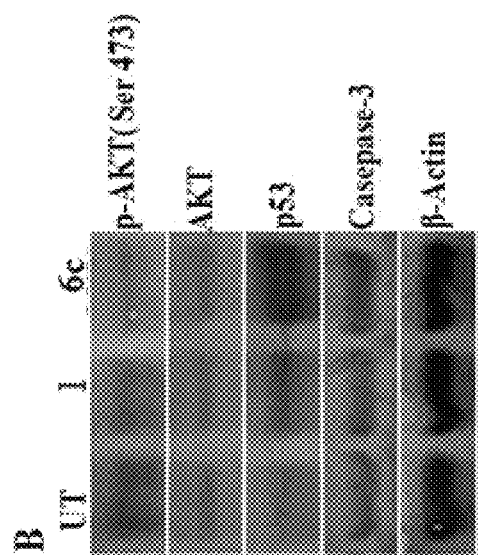

FIG. 5B: Western blot analysis with B16F10 tumor lysates: Differential expression of proteins.  denotes $p<0.01$; * $p<0.001$ while comparing with PR.

Figure 5C:
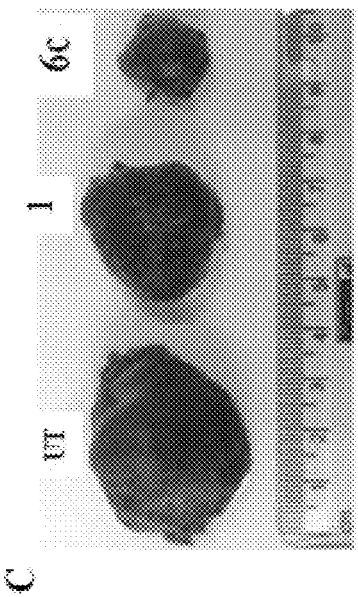

FIG. 5C: Representative tumors picture from sacrificed mice on day $25^{th}$.

Figure 6:
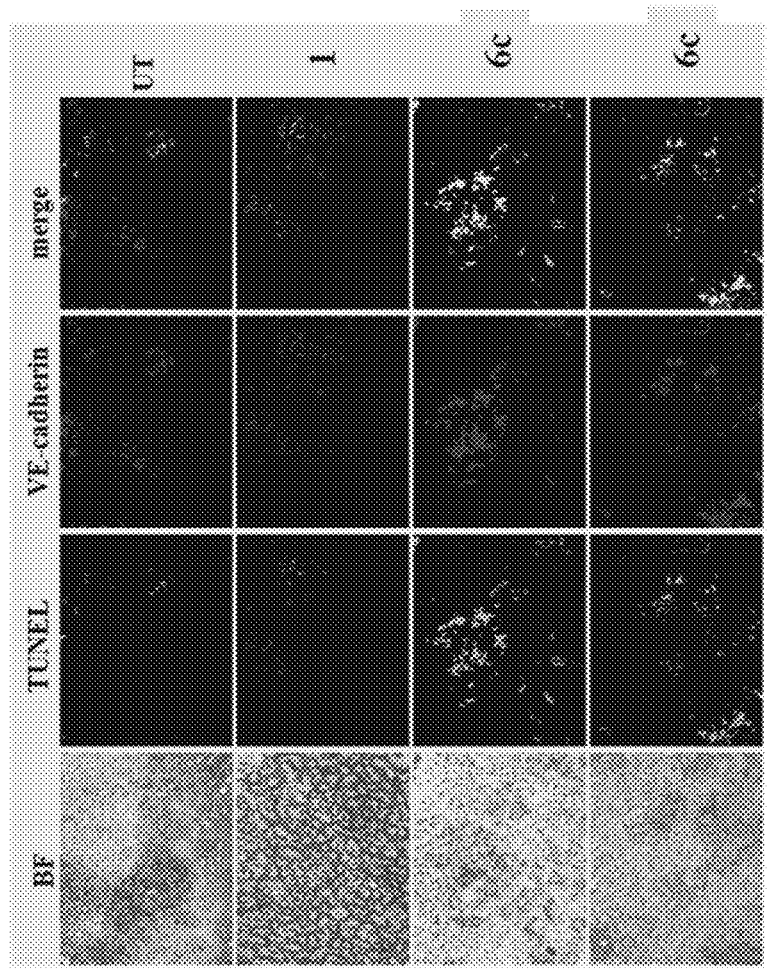

FIG. 6: Microscopic pictures with tumor sections obtained from UT (upper panel) group, compound 1 (second panel from top) and 6c (lower two panels) treated groups. From left the First column indicates the tissue in bright field (BF), second column represents the apoptotic region as obtained by TUNEL assay (green fluorescent), third column represents endothelial regions as stained by VE-Cadherin (red fluorescent), and fourth column represents merger of TUNEL and VE-cadherin panel. All images were taken at 10× magnification.

Figure 7A:
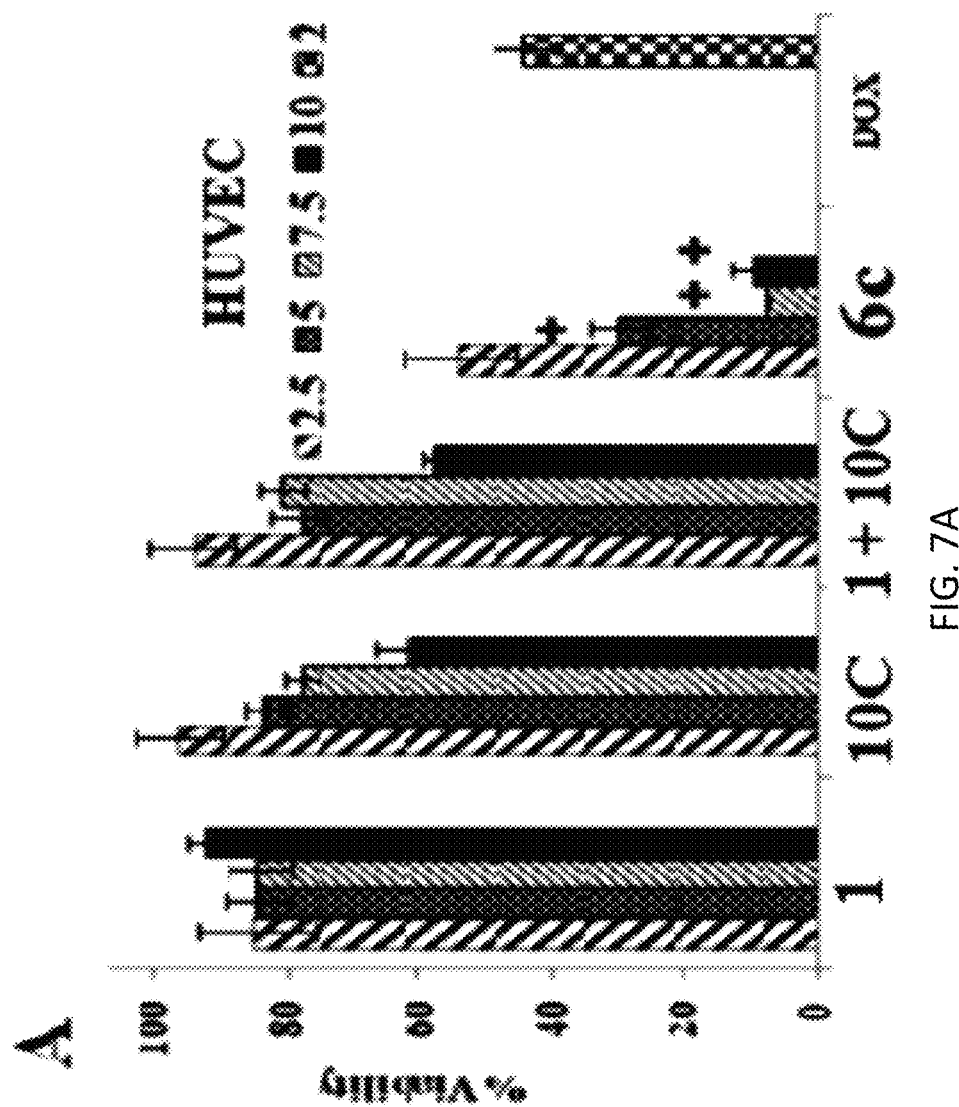

FIG. 7A: Viability study in HUVEC cell, following 48 h of treatment with compound 1, 10C, 1+10C and 6c at different concentration (10 μM, 7.5 μM, 5 μM and 2.5 μM) for 1+10C treatment both component was mixed at same concentration. 2 μM Doxorubicin (DOX) was taken as positive control. + indicates $p<0.01$.

Figure 7B:
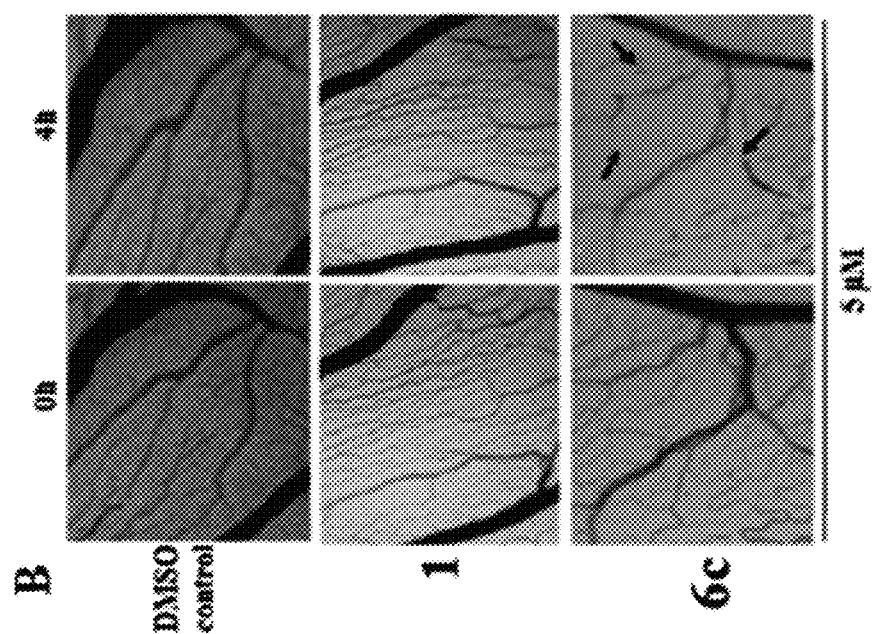

FIG. 7B: In vivo chick embryo angiogenesis (CEA) assay. Vascular sprouting was imaged following 0 h (left panel) and 4 h (right panel) treatment with DMSO, 1 (20 μL, 5 μM) and 6c (20 μL, 5 μM). Damaged vessel is indicated by black arrow.

ABBREVIATIONS

BAX: BCL-2 associated X protein
Bcl-2: B-cell lymphoma 2
BOC: Di-tert-butyl dicarbonate
CEA: Chick embryo angiogenesis
DCM: Dichloromethane
DIPEA: N,N-Diisopropylethylamine
DMSO: Dimethyl sulfoxide
EDCI: 1-Ethyl-3-(3-dimethylaminopropyl)carbodiimide
FACS: Fluorescence-activated cell sorting
FBS: Fetal bovine serum
FITC: Fluorescein isothiocyanate
HCl: Hydrochloric acid
HOBT: Hydroxybenzotriazole
HPLC: High Performance Liquid Chromatography
HUVEC: Human Umbilical Vein Endothelial Cells
EtOAc: Ethyl acetate
ESI-HRMS: Electrospray ionization-High resolution Mass Spectrometry
i.p.: Intraperitoneal
LiAlH$_4$: Lithium aluminium hydride Mdm2: Mouse double minute 2 homolog
MeOH: Methanol
MnO$_2$: Manganese dioxide
MTT: 3-(4,5-dimethylthiazol-2-yl)-2,5-diphenyltetrazolium bromide
Na$_2$SO$_4$: Sodium sulfate
NaHCO$_3$: Sodium bicarbonate
NMR: Nuclear magnetic resonance
PBS: Phosphate-buffered saline
PgR: Progesterone receptor
PI3K: Phosphatidylinositol-4,5-bisphosphate 3-kinase
PR: Progesterone
PTEN: Phosphatase and tensin homolog
RBF: Round bottom flask
RIPA: Radioimmunoprecipitation assay buffer
TFA: Trifluoroacetic acid
THF: Tetrahydrofuran
TUNEL: Terminal deoxynucleotidyl transferase dUTP nick end labeling

DETAILED DESCRIPTION OF THE INVENTION

The present invention relates to the development of a novel series of cationic lipid modified progesterone derivatives by chemically conjugating twin carbon chain-containing cationic lipids of varying chain lengths. The present invention discloses cytotoxicity study with 7 different cationic progesterone derivatives in wide range of cancer cells. This derivative showed minimal toxicity towards non-cancerous cell. This invention further demonstrated the cellular mechanism involved behind the anticancer activity by the most potent derivative. Overall the invention highlight the fact that chemical modification of progesterone can impart potent anticancer activity by co-inducing anti-angiogenesis and apoptosis irrespective of PgR expression profile.

The present invention discloses the process for the synthesis of a series of cationic lipid conjugated progesterone derivatives and subsequent evaluation of these compounds' anti-cancer activity in wide range of cancer cell. The present invention further provides the pre-clinical efficacy of the most potent derivative. Chemotherapy is likely to be the field where the present invention may be applicable.

The disclosed cationic progesterone compounds in this invention have certain common structural and functional groups which may be represented as general formula 6,

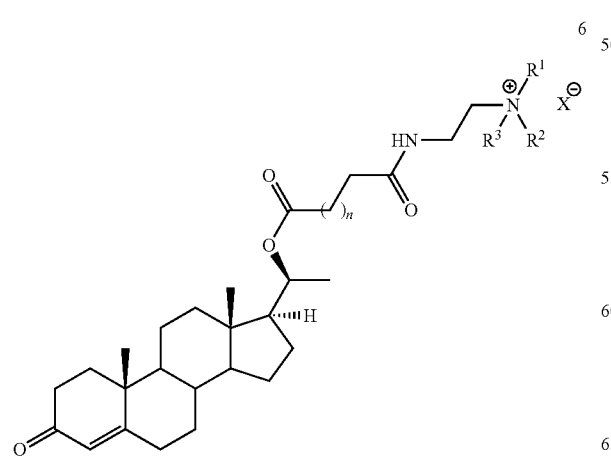

wherein: each of R$^1$ and R$^2$ is independently hydrogen or a lipophilic moiety containing a saturated alkyl chain, or a mono-, di- or tri-unsaturated alkenyl chain, each containing from 6 to 22 carbons, provided both R$^1$ and R$^2$ are not hydrogen; R$^3$ is independently a C$_1$-C$_5$ straight or branched chain alkyl group; n is an integer from 1 to 2; and X is selected from chlorine, bromine and iodine atom.

The present invention further provides a process for the preparation of compounds having general formula 6 and the said process comprising the steps of:

(a) reduction of progesterone with lithium aluminium hydride followed by regioselective oxidation by Manganese dioxide to get diastereoselective secondary alcohol intermediate with general formula 3 (MacNevin, C. J. et al. J. Med. Chem. 2009, 52, 6012-6023).

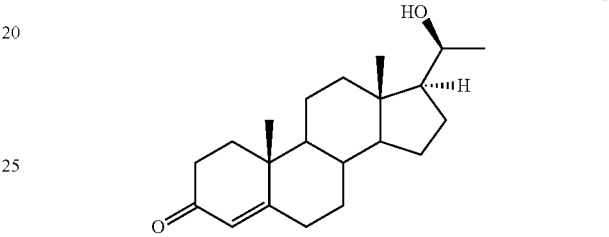

(b) introduction of spacer (n=1 to 2) using cyclic anhydride followed by coupling with N$^1$,N$^1$-di- or mono-alkylethane-1,2-diamine in the presence of coupling agent EDCI in dry solvent to obtain tertiary amine intermediate compound of general formula 5.

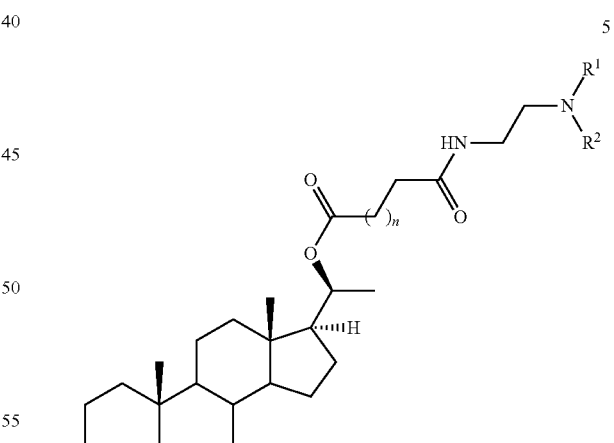

(c) the resultant tertiary amine is quaternized using alkyl halide in organic solvent followed by ion exchange chromatography using halide ion exchange resins to obtain the desired compound with general formula 6.

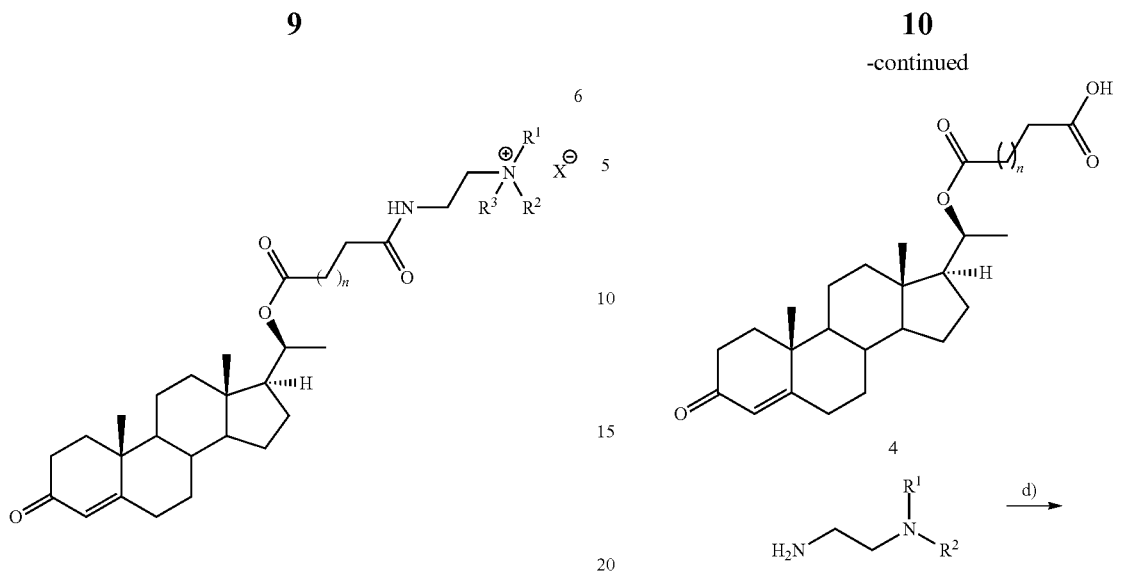

Scheme 1 general scheme for preparation of all the compounds.

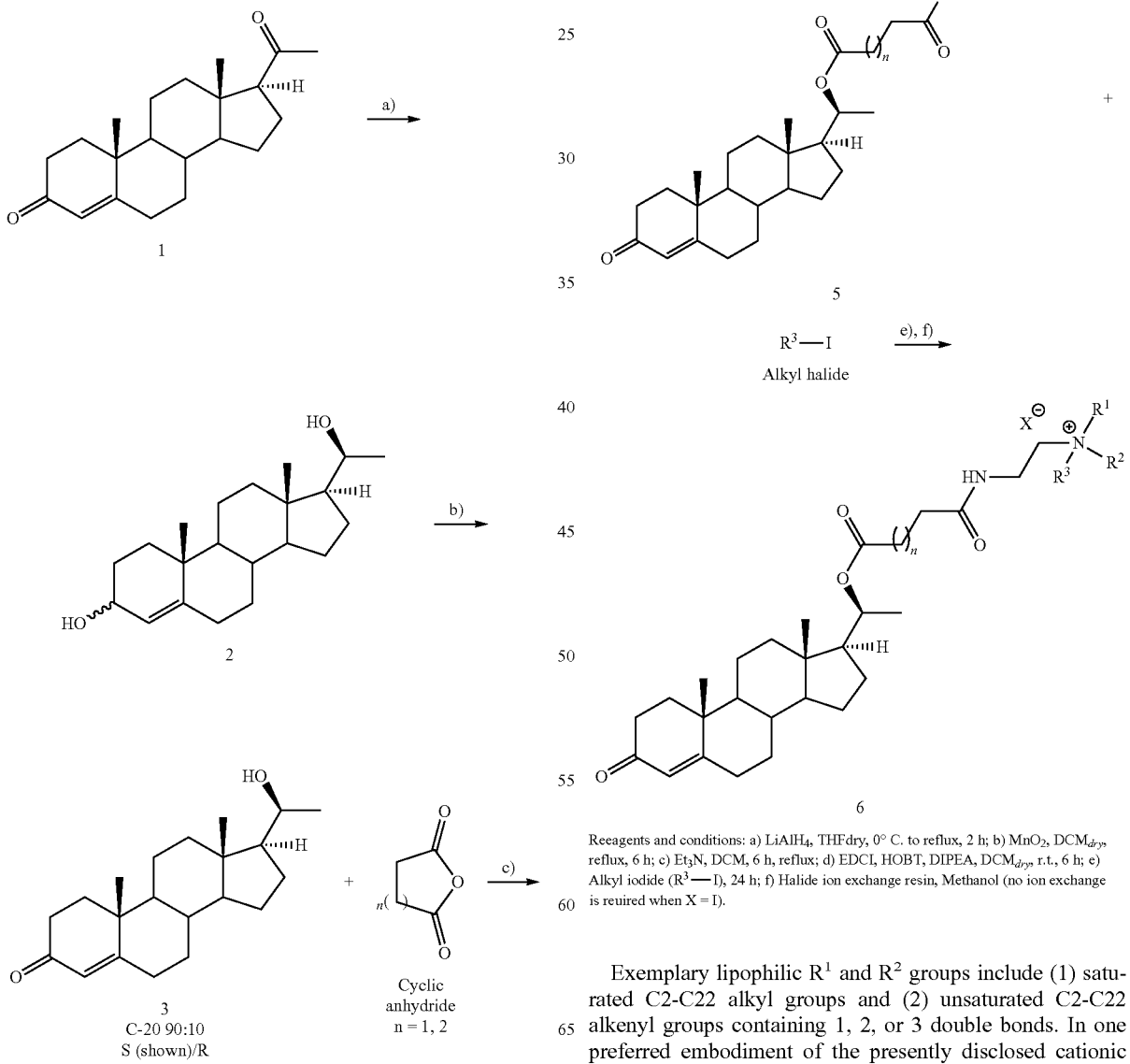

Reagents and conditions: a) LiAlH$_4$, THFdry, 0° C. to reflux, 2 h; b) MnO$_2$, DCM$_{dry}$, reflux, 6 h; c) Et$_3$N, DCM, 6 h, reflux; d) EDCI, HOBT, DIPEA, DCM$_{dry}$, r.t., 6 h; e) Alkyl iodide (R$^3$—I), 24 h; f) Halide ion exchange resin, Methanol (no ion exchange is required when X = I).

Exemplary lipophilic R$^1$ and R$^2$ groups include (1) saturated C2-C22 alkyl groups and (2) unsaturated C2-C22 alkenyl groups containing 1, 2, or 3 double bonds. In one preferred embodiment of the presently disclosed cationic lipids R$^1$=R$^2$=n-decyl, R$^3$ is a methyl, n=1, and X$^-$ is a chloride ion. Accordingly, the 6c is a representative example of the presently described novel cationic progesterone derivative:

Scheme 2 outlines the synthetic strategy employed for preparing the representative cationic Progesterone derivative 6c described in the present invention.

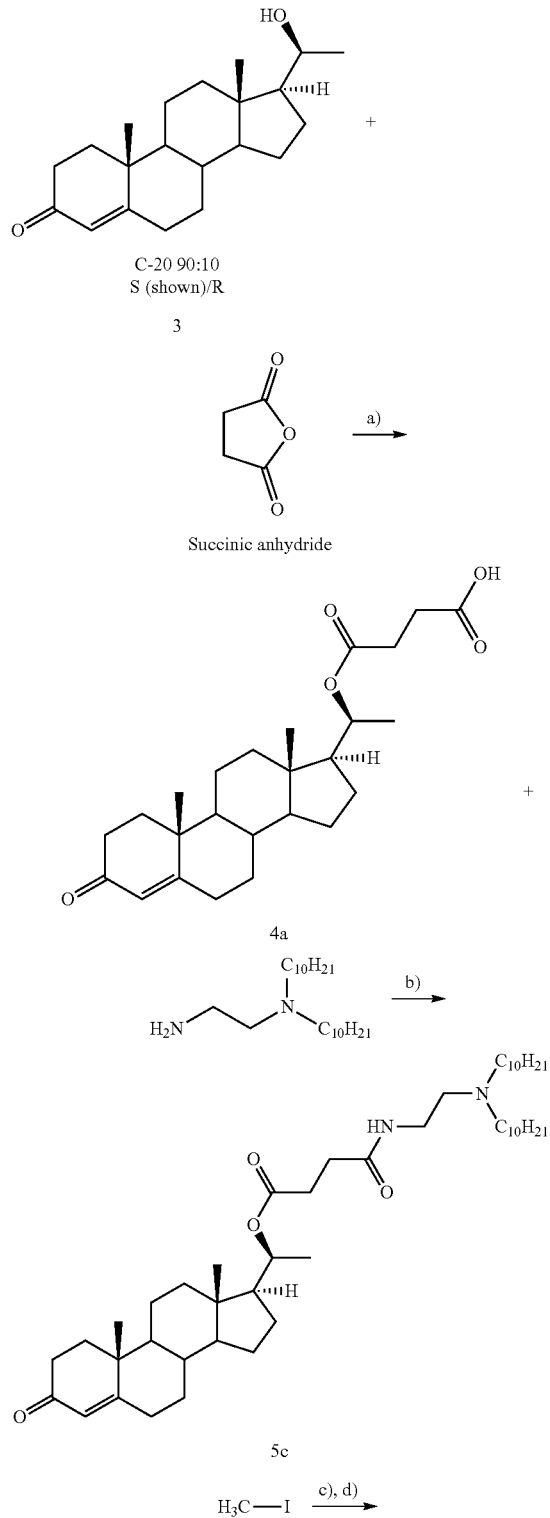

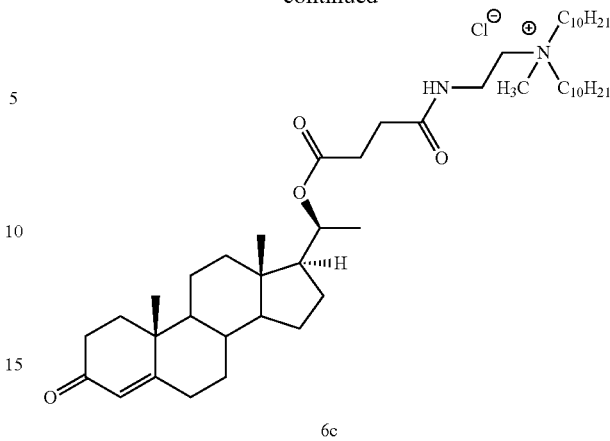

6c

Reagents and conditions: a) Et₃N, DCM, 6 h, reflux; b) EDCI, HOBT, DIPEA, DCM$_{dry}$, r.t., 6 h; c) Methyl iodide, 24 h; d) Chloride ion exchange resin, Methanol.

Applications

The process of the present invention can be used for preparing cationic lipid based progesterone derivatives. The newly developed novel cationic progesterone molecules described herein have the potential to prevent malignant progression through induction of apoptosis both in the tumor mass and its angiogenic vessels. The presently disclosed compounds are useful in treating wide range of cancers including breast, melanoma and ovarian cancer. The invention indicates that cationic progesterone derivative can inhibit PI3K/AKT survival pathway; hence the presently disclosed molecule can be used to sensitize the other drugs which become inactive due to over-activation of PI3K/AKT pathway. In summary, the presently invented cationic progesterone holds promising application in the field of anti-cancer therapy.

Cell Culture:

T47D, MCF-7, MDA-MB-231 (human breast carcinoma), OVCAR-3 (Human ovary carcinoma), B16F10 (murine melanoma), HUVEC (Human umbilical vein endothelium) cells were purchased from the American Type Cell Culture (ATCC, USA) and CHO (Chinese hamster ovary), NIH-3T3 (murine embryo fibroblast) and COS-1 (Kidney fibroblast) cells were purchased from National Center for Cell Sciences (Pune, India). All cells were grown into *mycoplasma* free condition. Apart from HUVEC cells which was cultured in complete EBM media containing 5% FBS, all remaining cells were either cultured in DMEM or RPMI (T47D) supplemented with 10% US origin FBS (Lonza, USA), 50 µg/mL penicillin, 50 µg/mL streptomycin and 100 µg/mL kanamycin at 37° C. in a humidified condition of 5% CO₂ in air. All cells were grown up to 75-85% confluency after which cells were trypsinized, counted and seeded, in 96-well plates for cell viability studies, 6-well plates for apoptosis studies, 60 mm dish for cell cycle studies and in 25 cm² or 75 cm² tissue culture flasks for Western blot studies.

Preparation of Samples:

The primary stock of the cationic progesterone molecules were made in cell culture grade DMSO and from that secondary stock was prepared by serial dilution with cell culture grade DMSO. The final working concentrations were prepared by diluting the secondary stock in cell culture media keeping the DMSO concentration in working solution below 0.2% with respect to cell culture medium.

Chemicals and General Procedures:

Porgesterone, EDTA, trypsin, cell culture media, 3-(4,5-dimethylthiazol-2-yl)-2,5-diphenyltetrazoliumbromide (MTT), propidium iodide (PI), FITC-labeled annexin V, RIPA buffer, dimethyl sulfoxide (DMSO) were purchased from Sigma Chemical Co. (St. Louis, Mo.). Fetal bovine serum (FBS) was purchased from Lonza, Swiss chemicals. RU486 purchased from calbiochem, Merch, USA. All other chemicals, reagents were purchased either from Sigma (St. Louis, Mo., USA) or from Rankem Ltd. (Mumbai, India). They were used without further purification. Lipofectamine 2000 was procured from Invitrogen Corporation (Carlsbad, Calif.). Reaction progress was monitored via thin-layer chromatography (TLC) on pre-coated glass-backed plates. All the intermediates were characterized by $^1$H NMR and mass spectrometry. The final molecules were characterized by $^1$H NMR, $^{13}$C NMR and ESI-HRMS and the purity was determined by HPLC. $^1$H and $^{13}$C NMR spectra were recorded on either a FT 300 or 500 MHz spectrometer in deuterated chloroform (CDCl3) and referenced to the residual solvent peak ($^1$H δ 7.27 ppm, $^{13}$C δ 77.23 ppm). Data for $^1$H NMR are reported as follows: chemical shift (δ in ppm), multiplicity (s=singlet, bs=broad singlet, d=doublet, t=triplet, m=multiplet), coupling constant (Hz), integration. ESI mass spectra were obtained using a QStar XL Hybrid QTOF mass spectrometer (Applied Biosystems). Purities of final products were determined in Varian ProStar HPLC instrument at 210 nm at a flow rate of 1 mL/min in a Varian Microsorb 100-10 BDS column (4.6 mm×250 mm) using MeOH as mobile phase.

The following examples are given by way of illustration of the present invention and therefore should not be construed to limit the scope of the present invention.

Example 1

Synthesis of N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-hexyl-N-methylhexan-1-aminium chloride, 6a (Scheme 1 & 2)

Step a) Synthesis of Pregn-4-ene-3,20-diol (20S) Compound 2 (Scheme 1)

Compound 2 and 3 were prepared according to MacNevin et. al. protocol. Briefly, an oven-dried RBF, fitted with a reflux condenser, was charged with 1.0 M solution of lithium aluminum hydride (20 mL, 20 mmol, 2.5 equiv) in THF and chilled in an ice bath. In a separate dry flask solution of progesterone (2.5 g, 8 mmol) was prepared in 20 mL dry THF. The progesterone solution was drop-wise added to the stirred lithium aluminum hydride solution at 0° C. Then the reaction mixture was heated under reflux for another 90 min. After completion, reaction mixture was cooled to room temperature, and quenched by the addition of ethyl acetate. The resultant mixture was dried by sodium sulphate. The organic filtrates were combined and concentrated to give 2.4 g (95% yields) of compound 2 as white crystalline solid.

$^1$H NMR (300 MHz, CDCl$_3$): δ 5.24 (d, J=1.5 Hz, 1H, C$_4$H), 4.13-4.06 (m, 1H, C$_3$H), 3.72-3.64 (m, 1H, C$_{20}$H), 2.25-0.68 (m, 22H), 1.13 (d, J=6.0 Hz, 3H, C$_{21}$H), 1.06 (s, 3H, C$_{19}$H), 0.77 (s, 3H, C$_{18}$H).

ESI-MS: m/z 283 ([M+H−2H$_2$O]$^+$, C$_{21}$H$_{31}$ requires 283.5); m/z 301 ([M+H—H$_2$O]$^+$, C$_{21}$H$_{33}$O requires, 301.4)

Step b) Synthesis of 20(S)-Hydroxypregn-4-en-3-one Compound 3 (Scheme 1)

An oven-dried 100 mL RBF, fitted with a reflux, was charged with crude compound 2 (1.2 g, 4 mmol) and freshly prepared manganese dioxide (7.0 g, 80 mmol, 20 equiv) in 40 mL of dry DCM. The mixture was heated to reflux and was continued for another 6 h. The mixture was then filtered through a pad of celite and rinsed with DCM. The clear, colorless filtrate was dried over anhydrous sodium sulfate followed by concentration to give an off-white solid. The solid was recrystallized from EtOAc/hexane to obtained 0.65 g (55% yield) of compound 3 as white solid; R$_f$=0.25 (1:1 EtOAc/hexane).

$^1$H NMR (300 MHz, CDCl$_3$): δ 5.68 (s, 1H, C$_4$H), 3.72-3.67 (m, 1H, C$_{20}$H), 2.43-0.9 (m, 21H), 1.19 (s, 3H, C$_{19}$H), 1.13 (d, J=6.0 Hz, 3H, C$_{21}$H), 0.79 (s, 3H, C$_{18}$H).

$^{13}$C NMR (300 MHz, CDCl3): δ 199.6, 171.5, 123.7, 70.3, 58.2, 55.2, 53.8, 42.3, 39.6, 38.4, 35.6, 35.3, 33.8, 32.8, 32.0, 25.5, 24.4, 23.7, 20.8, 17.4, 12.3.

ESI-MS: m/z 317 ([M+H]$^+$, C$_{21}$H$_{33}$O$_2$ requires 317.4).

Step c) Synthesis of Compound 4a (Scheme 2)

Compound 3 (0.5 g, 1.58 mmol) was added to a 25 mL RBF, already containing succinic anhydride (0.237 g, 2.37 mmol, 1.5 equiv), di-isopropylethylamine (160 uL, 0.95 mmol, 0.6 equiv) in 10 mL dry DCM under nitrogen atmosphere. The mixture was refluxed for 12 h followed by cooling to room temperature. After cooling, the reaction mixture was poured into 20 mL DCM, washed with 1N HCl (3×20 ml) and then with brine (3×20 ml), dried over anhydrous Na$_2$SO$_4$ and evaporated to give off-white solid. The obtained mixture was subjected to separation on column chromatography using mixture of methanol-chloroform (0.4-0.7%, v/v) to get 0.59 g (90% yield) white solid (R$_f$=0.50 in 5% methanol-chloroform, v/v).

$^1$H NMR (300 MHz, CDCl$_3$): δ 5.67 (s, 1H, C$_4$H), 4.88-4.81 (m, 1H, C$_{20}$H), 2.88-0.7 (m, 25H), 1.16 (s, 3H, C$_{19}$H), 1.12 (d, J=5.86 Hz, 3H, C$_{21}$H), 0.64 (s, 3H, C$_{18}$H).

ESI-MS: m/z 417 ([M+H]$^+$, C$_{25}$H$_{37}$O$_5$ requires 417.5); m/z 439 ([M+Na]$^+$, C$_{25}$H$_{36}$O$_5$Na requires 439.5).

Step d) Synthesis of Compound 5a

Compound 4a (0.3 g, 0.72 mmol) was dissolved in 10 ml of dry dichloromethane (DCM) in a 25 ml RBF and stirred over for 15 min at 0° C. To above reaction mixture, 1-Ethyl-3-(3-dimethylaminopropyl)carbodiimide (EDCI) (0.137 g, 0.72 mmol, 1 equiv) and Hydroxybenzotriazole (HOBT) (0.110 g, 0.72 mmol, 1 equiv) were added, and stirring was continued for another 30 min to activate the acid group. In a separate flask N$^1$,N$^1$-dihexylethane-1,2-diamine (0.214 g, 0.93 mmol, 1.3 equiv) was dissolved in 2 mL dry DCM followed by addition of di-isopropylethylamine (DIPEA) until the reaction mixture became slightly basic. Then the resulting solution was added to the above activated acid solution and the reaction was continued for 6 h. Then the reaction mixture was poured into 30 ml of DCM, washed with 1N HCl (3×20 ml), saturated NaHCO$_3$ solution (3×20 ml) and brine (3×20 ml), dried with anhydrous Na$_2$SO$_4$ and the organic layer was concentrated. The crude was purified by column chromatography using 60-120 mesh silica gel and the compound was eluted using methanol-chloroform eluent (0.25%-0.4%, v/v) yielded compound 5a as a yellow gummy product. (0.31 g, 70% yield, $R_f$=0.55 in 5% methanol-chloroform, v/v). $^1$H NMR (300 MHz, CDCl$_3$): δ 5.72 (s, 1H, C$_4$H), 4.86-4.81 (m, 1H, C$_{20}$H), 3.02-2.72 (m, 4H), 2.62-2.52 (m, 4H), 2.45-0.92 (m, 40H), 1.17 (s, 3H, C$_{19}$H), 1.15 (d, J=6.1 Hz, 3H, C$_{21}$H), 0.88 [t, J=6.9 Hz, 6H, —N(—CH$_2$—CH$_2$—(CH$_2$)$_3$—CH$_3$)$_2$], 0.66 (s, 3H, C$_{18}$H).

ESI-MS: m/z 628 ([M+H]$^+$, C$_{39}$H$_{67}$O$_4$N$_2$ requires 627.9).

Step e) and f) Synthesis of Compound 6a

Compound 5a (0.1 g, 0.16 mmol) was treated with excess methyl iodide (5 mL) and stirred for 24 h at room temperature. After that the reaction mixture was filtered, concentrated and the residue was purified by column chromatographic purification (using 100 to 200 mesh size silica gel and 1.0-1.3% methanol in chloroform was used as eluent) to give yellowish gummy solid compound which was then passed through chloride ion exchange chromatography (using Amberlite IRA-400Cl resin and methanol as eluent) yielded compound 6a as a yellowish gummy solid (0.06 g, 55% yield, $R_f$=0.2 in 10% methanol chloroform, v/v).

$^1$H NMR (300 MHz, CDCl$_3$): δ 8.07 (bs, 1H, —N—H), 5.67 (s, 3H, C$_{19}$H), 4.8-4.76 (m, 1H, C$_{20}$H), 3.78-3.74 (m, 4H), 3.53-3.49 (m, 4H), 3.37 (s, 3H, —OC—HN—CH$_2$—CH$_2$—N—CH$_3$), 2.57-0.97 (m, 40H), 1.19 (s, 3H, C$_{19}$H), 1.14 (d, J=5.9 Hz, 3H, C$_{21}$H), 0.93 [t, J=6.9 Hz, 6H, —N(—CH$_2$—CH$_2$—(CH$_2$)$_3$—CH$_3$)$_2$], 0.66 (s, 3H, C$_{18}$H).

$^{13}$C NMR (300 MHz, CDCl3): δ 199.6, 172.8, 171.9, 171.4, 123.7, 72.8, 62.3, 60.6, 55.1, 54.8, 53.7, 49.2, 44.8, 42.1, 38.9, 38.5, 35.6, 35.4, 33.9, 33.7, 32.8, 31.9, 31.2, 30.4, 29.6, 29.4, 29.2, 25.9, 25.3, 24.1, 22.3, 20.9, 19.8, 17.3, 13.8, 12.4.

ESI-HRMS: m/z 641.3239 ([M-Cl]$^+$, C$_{40}$H$_{69}$O$_4$N$_2$ requires 641.3239).

HPLC purity >96%

Example 2

Synthesis of N-(2-(4-(((1S)-1-(((10R,13S,17S)-10,13-dimethyl-3-oxo-2,3,6,7,8,9,10,11,12, 13,14, 15,16, 17-tetradecahydro-1H-cyclopenta[a]phenanthren-17-yl)ethoxy)-4-oxobutanamido)ethyl)-N-methyl-N-octyloctan-1-aminium chloride, 6b Step d) Synthesis of Compound 5b The Compound 4a (0.35 g, 0.84 mmol) obtained in step c (example 1) was dissolved in 12 ml of dry dichloromethane (DCM) in a 25 ml RBF and stirred for 15 min at 0° C. To above reaction mixture, 1-Ethyl-3-(3-dimethylaminopropyl)carbodiimide (EDCI) (0.159 g, 0.84 mmol, 1 equiv) and Hydroxybenzotriazole (HOBT) (0.128 g, 0.84 mmol, 1 equiv) were added, and stirring was continued for another 30 min to activate the acid group. In a separate flask N$^1$,N$^1$-dioctylethane-1,2-diamine (0.310 g, 1.09 mmol, 1.3 equiv) was dissolved in 2 mL dry DCM followed by addition of di-isopropylethylamine (DIPEA) until the reaction mixture became slightly basic. Then the resulting solution was added to the above activated acid solution and the reaction was continued for 6 h. Following 6 h reaction mixture was poured into 30 ml of DCM, washed with 1N HCl (3×20 ml), saturated NaHCO$_3$ solution (3×20 ml) and brine (3×20 ml), dried with anhydrous Na$_2$SO$_4$ and the organic layer concentrated. Then the crude was purified by column chromatography using 60-120 mesh silica gel and the compound was eluted using methanol-chloroform eluent (0.25%-0.4%, v/v) yielded compound 5b as a yellow gummy product. (0.365 g, 64% yield, $R_f$=0.55 in 5% methanol-chlororform, v/v).

$^1$H NMR (300 MHz, CDCl$_3$): δ 8.06 (bs, 1H, N—H), 5.73 (s, 1H, C$_4$H), 4.88-4.80 (m, 1H, C$_{20}$H), 2.99-2.87 (m, 4H), 2.61-2.52 (m, 4H), 2.46-0.91 (m, 48H), 1.17 (s, 3H, C$_{19}$H), 1.14 (d, J=6.0 Hz, 3H, C$_{21}$H), 0.88 [t, J=6.9 Hz, 6H, —N(—CH$_2$—CH$_2$—(CH$_2$)$_3$—CH$_3$)$_2$], 0.66 (s, 3H, C$_{18}$H).

ESI-MS: m/z 684 ([M+H]$^+$, C$_{43}$H$_{75}$O$_4$N$_2$ requires 684.0).

Step e) f) Synthesis of Compound 6b

Compound 5b (0.1 g, 0.15 mmol) was dissolved in excess methyl iodide (5 mL) and stirred for 24 h at room temperature. After that the reaction mixture was filtered, concentrated and the residue was purified by column chromatographic purification (using 100 to 200 mesh size silica gel and 1.0-1.4% methanol in chloroform was used as eluent) to give yellowish gummy solid compound which was then passed through chloride ion exchange chromatography (using Amberlite IRA-400Cl resin and methanol as eluent) yielded compound 6b as a yellowish gummy solid (0.055 g, 52.5% yield, $R_f$=0.2 in 10% methanol-chloroform, v/v).

$^1$H NMR (300 MHz, CDCl$_3$): δ 8.63 (bs, 1H, —N—H), 5.67 (s, 3H, C$_{19}$H), 4.784-4.753 (m, 1H, C$_{20}$H), 3.72-3.58 (m, 4H), 3.35-3.33 (m, 4H), 3.18 (s, 3H, —OC—HN—CH$_2$—CH$_2$—N—CH$_3$), 2.58- 0.94 (m, 48H), 1.18 (s, 3H, C$_{19}$H), 1.12 (d, J=6.0 Hz, 3H, C$_{21}$H), 0.88 [t, J=7.0 Hz, 6H, —N(—CH$_2$—CH$_2$—(CH$_2$)$_3$—CH$_3$)$_2$], 0.66 (s, 3H, C$_{18}$H).

$^{13}$C NMR (300 MHz, CDCl3): δ 199.6, 173.0, 171.9, 171.5, 123.7, 72.8, 62.3, 60.6, 55.1, 54.8, 53.7, 48.7, 42.1, 38.9, 38.5, 35.6, 35.4, 33.9, 33.7, 32.8, 31.9, 31.6, 30.2, 29.4, 29.2, 29.1, 29.0, 26.3, 25.3, 24.1, 22.5, 22.3, 20.9, 19.8, 17.3, 14.0, 12.4.

ESI-HRMS: m/z 697.5855 ([M-Cl]$^+$, C$_{44}$H$_{77}$O$_4$N$_2$ requires 697.5877).

HPLC purity >97%

Example 3

Synthesis of N-decyl-N-(2-(4-(((1S)-1-(((10R,13S, 17S)-10,13-dimethyl-3-oxo-2,3,6,7,8,9,10,11,12,13, 14,15,16,17-tetradecahydro-1H-cyclopenta[a] phenanthren-17-yl)ethoxy)-4-oxobutanamido) ethyl)-N-methyldecan-1-aminium chloride 6c Step d) Synthesis of Compound 5c In a 25 ml RBF Compound 4a (0.3 g, 0.72 mmol) was dissolved in 10 ml of dry dichloromethane (DCM) and stirred for 15 min at 0° C. To activate the acid group, 1-Ethyl-3-(3-dimethylaminopropyl)carbodiimide (EDCI) (0.137 g, 0.72 mmol, 1 equiv) and Hydroxybenzotriazole (HOBT) (0.110 g, 0.72 mmol, 1 equiv) were added to the above reaction mixture, and stirring was continued for another 30 min. In a separate flask N$^1$,N$^1$-didecylethane-1, 2-diamine (0.318 g, 0.93 mmol, 1.3 equiv) was dissolved in 2 mL dry DCM and to that di-isopropylethylamine (DIPEA) was added until the reaction mixture became slightly basic. Then the resulting solution was added to the above activated acid solution and the reaction was continued for 6 h. After that reaction mixture was poured into 30 ml of DCM, washed with 1N HCl (3×20 ml), saturated NaHCO$_3$ solution (3×20 ml) and brine (3×20 ml), dried with anhydrous Na$_2$SO$_4$ and the organic layer concentrated. Then the crude was purified by column chromatography using 60-120 mesh silica gel and the compound was eluted using methanol-chloroform eluent (0.25%-0.35%, v/v) yielded compound 5c as a yellow gummy product. (0.357 g, 67% yield, $R_f$=0.60 in 5% methanol-chlororform, v/v).

$^1$H NMR (300 MHz, CDCl$_3$): δ 7.67 (bs, 1H, N—H), 5.72 (s, 1H, C$_4$H), 4.86-4.80 (m, 1H, C$_{20}$H), 2.92-2.87 (m, 4H), 2.61-2.53 (dd, 4H, J=5.6, 17.2 Hz), 2.43-0.92 (m, 56H), 1.17 (s, 3H, C$_{19}$H), 1.15 (d, J=6.0 Hz, 3H, C$_{21}$H), 0.88 [t, J=6.6 Hz, 6H, —N(—CH$_2$—CH$_2$—(CH$_2$)$_3$—CH$_3$)$_2$], 0.66 (s, 3H, C$_{18}$H).

ESI-MS: m/z 740 ([M+H]$^+$, C$_{47}$H$_{83}$O$_4$N$_2$ requires 740.1).

Step e) and f) Synthesis of Compound 6c

Compound 5c (0.1 g, 0.14 mmol) was treated with excess methyl iodide (5 mL) and stirred for 24 h at room temperature. After that the reaction mixture was filtered, concentrated and the residue was purified by column chromatographic purification (using 100 to 200 mesh size silica gel and 1.0-1.5% methanol in chloroform was used as eluent) to give yellowish gummy solid compound which was then passed through chloride ion exchange chromatography (using Amberlite IRA-400Cl resin and methanol as eluent) yielded compound 6c as a yellowish gummy solid. (0.06 g, 58.6% yield, $R_f$=0.2 in 10% methanol-chloroform, v/v).

$^1$H NMR (300 MHz, CDCl$_3$): δ 8.63 (bs, 1H, —N—H), 5.71 (s, 3H, C$_{19}$H), 4.82-4.75 (m, 1H, C$_{20}$H), 3.77-3.58 (m, 4H), 3.32-3.26 (m, 4H), 3.16 (s, 3H, —OC—HN—CH$_2$—CH$_2$—N—CH$_3$), 2.56- 0.98 (m, 56H), 1.18 (s, 3H, C$_{19}$H), 1.12 (d, J=6.0 Hz, 3H, C$_{21}$H), 0.88 [t, J=6.8 Hz, 6H, —N(—CH$_2$—CH$_2$—(CH$_2$)$_3$—CH$_3$)$_2$], 0.66 (s, 3H, C$_{18}$H).

$^{13}$C NMR (300 MHz, CDCl3): δ 199.6, 173.2, 172.0, 171.4, 123.7, 72.9, 62.4, 60.7, 55.1, 54.8, 53.7, 48.8, 42.1, 38.8, 38.5, 35.6, 35.4, 33.9, 33.7, 32.8, 31.9, 31.8, 30.2, 29.4, 29.3, 29.2, 29.1, 26.3, 25.3, 24.2, 22.6, 22.3, 20.9, 19.8, 17.3, 14.1, 12.4.

ESI-HRMS: m/z 753.6508 ([M-Cl]$^+$, C$_{48}$H$_{85}$O$_4$N$_2$ requires 753.6503).

HPLC purity >98%

Example 4

Synthesis of N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-dodecyl-N-methyldodecan-1-aminium chloride 6d Step d) Synthesis of Compound 5d Compound 4a (0.3 g, 0.72 mmol) was dissolved in 10 ml of dry dichloromethane (DCM) and stirred for 15 min at 0° C. To the above reaction mixture, 1-Ethyl-3-(3-dimethylaminopropyl) carbodiimide (EDCI) (0.137 g, 0.72 mmol, 1 equiv) and Hydroxybenzotriazole (HOBT) (0.110 g, 0.72 mmol, 1 equiv) was added, and stirring was continued for another 30 min to activate the acid group. In a separate flask N$^1$,N$^1$-didodecylethane-1,2-diamine (0.37 g, 0.93 mmol, 1.3 equiv) was dissolved in 2 mL dry DCM followed by addition of di-isopropylethylamine (DIPEA) until the reaction mixture became slightly basic. Then the resulting solution was added to the above activated acid solution and the reaction was continued for 6 h. Then the reaction mixture was poured into 30 ml of DCM, washed with 1N HCl (3×20 ml), saturated NaHCO$_3$ solution (3×20 ml) and brine (3×20 ml), dried with anhydrous Na$_2$SO$_4$ and the organic layer concentrated. After that crude was purified by column chromatography using 60-120 mesh silica gel and the compound was eluted using methanol-chloroform eluent (0.25%-0.4%, v/v) yielded compound 5d as a yellow gummy product. (0.367 g, 64% yield, $R_f$=0.60 in 5% methanol-chloroform, v/v).

$^1$H NMR (300 MHz, CDCl$_3$): δ 8.4 (bs, 1H, N—H), 5.72 (s, 1H, C$_4$H), 4.82-4.76 (m, 1H, C$_{20}$H), 3.2-3.04 (m, 4H), 2.61-2.53 (m, 4H), 2.43-0.92 (m, 64H), 1.17 (s, 3H, C$_{19}$H), 1.15 (d, J=6.0 Hz, 3H, C$_{21}$H), 0.88 [t, J=7.5 Hz, 6H, —N(—CH$_2$—CH$_2$—(CH$_2$)$_3$—CH$_3$)$_2$], 0.66 (s, 3H, C$_{18}$H).

ESI-MS: m/z 796 ([M+H]$^+$, C$_{51}$H$_{91}$O$_4$N$_2$ requires 796.2).

Step e) f) Synthesis of Compound 6d

Compound 5d (0.1 g, 0.13 mmol) was reacted with excess methyl iodide (5 mL) for 24 h at room temperature. After that the reaction mixture was filtered, concentrated and the residue was purified by column chromatographic purification (using 100 to 200 mesh size silica gel and 1.0-1.3% methanol in chloroform was used as eluent) to give gummy solid compound which was then passed through chloride ion exchange chromatography (using Amberlite IRA-400Cl resin and methanol as eluent) yielded compound 6d as a yellowish gummy solid. (0.064 g, 61% yield, $R_f$=0.2 in 10% methanol-chloroform, v/v).

$^1$H NMR (300 MHz, CDCl$_3$): δ 9.13 (bs, 1H, —N—H), 5.72 (s, 3H, C$_{19}$H), 4.82-4.77 (m, 1H, C$_{20}$H), 3.83-3.65 (m, 4H), 3.39-3.33 (m, 4H), 3.30 (s, 3H, —OC—HN—CH$_2$—CH$_2$—N—CH$_3$), 2.59- 0.93 (m, 64H), 1.17 (s, 3H, C$_{19}$H), 1.13 (d, J=6.0 Hz, 3H, C$_{21}$H), 0.88 [t, J=6.4 Hz, 6H, —N(—CH$_2$—CH$_2$—(CH$_2$)$_3$—CH$_3$)$_2$], 0.66 (s, 3H, C$_{18}$H).

$^{13}$C NMR (300 MHz, CDCl3): δ 199.6, 172.9, 172.0, 171.4, 123.7, 72.8, 62.2, 60.7, 55.1, 54.8, 53.7, 49.2, 42.2, 38.9, 38.5, 35.6, 35.4, 33.9, 33.6, 32.8, 31.9, 31.8, 30.4, 29.5, 29.4, 29.3, 29.2, 29.1, 26.3, 25.3, 24.1, 22.6, 22.3, 20.9, 19.8, 17.3, 14.0, 12.4.

ESI-HRMS: m/z 809.7108 ([M-Cl]$^+$, C$_{52}$H$_{93}$O$_4$N$_2$ requires 809.7129).

HPLC purity >98%

Example 5

Synthesis of N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-methyl-N-tetradecyltetradecan-1-aminium chloride 6e Step d) Synthesis of Compound 5e Compound 4a (0.25 g, 0.60 mmol) was dissolved in 8 ml of dry dichloromethane (DCM) and stirred for 15 min at 0° C. To the above reaction mixture, 1-Ethyl-3-(3-dimethylaminopropyl) carbodiimide (EDCI) (0.114 g, 0.60 mmol, 1 equiv) and Hydroxybenzotriazole (HOBT) (0.092 g, 0.60 mmol, 1 equiv) was added, and stirring was continued for another 30 min to activate the acid group. In a separate flask N$^1$,N$^1$-ditetradecylethane-1,2-diamine (0.352 g, 0.78 mmol, 1.3 equiv) was dissolved in 2 mL dry DCM followed by addition of di-isopropylethylamine (DIPEA) until the reaction mixture became slightly basic. Then the resulting solution was added to the above activated acid solution and the reaction was continued for 6 h. After completion of the reaction, resultant mixture was poured into 20 ml of DCM, washed with 1N HCl (3×20 ml), saturated NaHCO$_3$ solution (3×20 ml) and brine (3×20 ml), dried with anhydrous Na$_2$SO$_4$ and the organic layer concentrated. Then the crude was purified by column chromatography using 60-120 mesh silica gel and the compound was eluted using methanol-chloroform eluent (0.25%-0.5%, v/v) yielded compound 5e as a yellow gummy product. (0.357 g, 71% yield, $R_f$=0.66 in 5% methanol-chlororform, v/v). $^1$H NMR (300 MHz, CDCl$_3$): δ 8.4 (bs, 1H, N—H), 5.72 (s, 3H, C$_{19}$H), 4.86-4.77 (m, 1H, C$_{20}$H), 3.19-3.02 (m, 4H), 2.59-2.51 (m, 4H), 2.44-0.92 (m, 72H), 1.17 (s, 3H, C$_{19}$H), 1.13 (d, J=6.0 Hz, 3H, C$_{21}$H), 0.88 [t, J=6.6 Hz, 6H, —N(—CH$_2$—CH$_2$—(CH$_2$)$_3$—CH$_3$)$_2$], 0.66 (s, 3H, C$_{18}$H).

ESI-MS: m/z 852 ([M+H]$^+$, C$_{55}$H$_{99}$O$_4$N$_2$ requires 852.4).

Step e) f) Synthesis of Compound 6e

Compound 5e (0.120 g, 0.14 mmol) was reacted with excess methyl iodide (5 mL) and stirred for 24 h at room temperature. After that the reaction mixture was filtered, concentrated and the residue was purified by column chromatographic purification (using 100 to 200 mesh size silica gel and 1.0-1.25% methanol in chloroform was used as eluent) to give gummy solid compound which was then passed through chloride ion exchange chromatography (using Amberlite IRA-400Cl resin and methanol as eluent) yielded compound 6e as a yellowish gummy solid. (0.07 g, 56% yield, $R_f$=0.2 in 10% methanol-chloroform, v/v).

$^1$H NMR (300 MHz, CDCl$_3$): δ 9.09 (bs, 1H, —N—H), 5.72 (s, 3H, C$_{19}$H), 4.84-4.75 (m, 1H, C$_{20}$H), 3.78-3.65 (m, 4H), 3.39-3.33 (m, 4H), 3.30 (s, 3H, —OC—HN—CH$_2$—CH$_2$—N—CH$_3$), 2.59- 0.93 (m, 72H), 1.17 (s, 3H, C$_{19}$H), 1.13 (d, J=6.0 Hz, 3H, C$_{21}$H), 0.88 [t, J=6.6 Hz, 6H, —N(—CH$_2$—CH$_2$—(CH$_2$)$_3$—CH$_3$)$_2$], 0.66 (s, 3H, C$_{18}$H).

$^{13}$C NMR (300 MHz, CDCl3): δ 199.5, 172.8, 172.0, 171.4, 123.7, 72.7, 62.2, 60.6, 55.1, 54.7, 53.7, 49.1, 42.1, 38.8, 38.5, 35.5, 35.3, 33.9, 33.6, 32.8, 31.8, 30.3, 29.5, 29.2, 29.1, 29.0, 26.3, 25.3, 24.1, 22.5, 22.3, 20.8, 19.7, 17.2, 14.0, 12.3.

ESI-HRMS: m/z 865.7725 ([M-Cl]$^+$, C$_{56}$H$_{101}$O$_4$N$_2$ requires 865.7755).

HPLC purity >98%

Example 6

Synthesis of N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-hexadecyl-N-methylhexadecan-1-aminium chloride 6f Step d) Synthesis of Compound 5f Compound 4a (0.25 g, 0.60 mmol) was dissolved in 10 ml of dry dichloromethane (DCM) and stirred for 15 min at 0° C. To the above reaction mixture, 1-Ethyl-3-(3-dimethylaminopropyl) carbodiimide (EDCI) (0.114 g, 0.60 mmol, 1 equiv) and Hydroxybenzotriazole (HOBT) (0.092 g, 0.60 mmol, 1 equiv) was added, and stirring was continued for another 30 min to activate the acid group. In a separate flask N$^1$,N$^1$-dihexadecylethane-1,2-diamine (0.397 g, 0.78 mmol, 1.3 equiv) was dissolved in 2 mL dry DCM followed by addition of di-isopropylethylamine (DIPEA) until the reaction mixture became slightly basic. Then the resulting solution was added to the above activated acid solution and the reaction was continued for 6 h. Then the reaction mixture was poured into 20 ml of DCM, washed with 1N HCl (3×20 ml), saturated NaHCO$_3$ solution (3×20 ml) and brine (3×20 ml), dried with anhydrous Na$_2$SO$_4$ and the organic layer concentrated. Then the crude was purified by column chromatography using 60-120 mesh silica gel and the compound was eluted using methanol-chloroform eluent (0.25%-0.4%, v/v) yielded compound 5f as a yellow gummy product. (0.321 g, 59% yield, $R_f$=0.65 in 5% methanol-chlororform, v/v).

$^1$H NMR (300 MHz, CDCl$_3$): δ 8.3 (bs, 1H, N—H), 5.72 (s, 3H, C$_{19}$H), 4.86-4.79 (m, 1H, C$_{20}$H), 3.15-3.03 (m, 4H), 2.60-2.59 (m, 4H), 2.49-0.93 (m, 80H), 1.17 (s, 3H, C$_{19}$H), 1.13 (d, J=6.0 Hz, 3H, C$_{21}$H), 0.88 [t, J=6.3 Hz, 6H, —N(—CH$_2$—CH$_2$—(CH$_2$)$_3$—CH$_3$)$_2$], 0.66 (s, 3H, C$_{18}$H).

ESI-MS: m/z 908 ([M+H]$^+$, C$_{59}$H$_{107}$O$_4$N$_2$ requires 908.4).

Step e) f) Synthesis of Compound 6f

Compound 5f (0.120 g, 0.13 mmol) was reacted with excess methyl iodide (5 mL) and stirred for 24 h at room temperature. After that the reaction mixture was filtered, concentrated and the residue was purified by column chromatographic purification (using 100 to 200 mesh size silica gel and 1.0-1.3% methanol in chloroform was used as eluent) to give gummy solid compound which was then passed through chloride ion exchange chromatography (using Amberlite IRA-400Cl resin and methanol as eluent) yielded compound 6f as a yellowish gummy solid. (0.06 g, 51% yield, $R_f$=0.25 in 10% methanol-chloroform, v/v).

$^1$H NMR (300 MHz, CDCl$_3$): δ 8.89 (bs, 1H, —N—H), 5.72 (s, 3H, C$_{19}$H), 4.83-4.74 (m, 1H, C$_{20}$H), 3.76-3.66 (m, 4H), 3.38-3.33 (m, 4H), 3.27 (s, 3H, —OC—HN—CH$_2$—CH$_2$—N—CH$_3$), 2.56- 0.93 (m, 80H), 1.18 (s, 3H, C$_{19}$H), 1.13 (d, J=6.0 Hz, 3H, C$_{21}$H), 0.88 [t, J=6.4 Hz, 6H, —N(—CH$_2$—CH$_2$—(CH$_2$)$_3$—CH$_3$)$_2$], 0.66 (s, 3H, C$_{18}$H).

$^{13}$C NMR (300 MHz, CDCl3) δ 199.5, 172.8, 172.0, 171.3, 123.7, 72.8, 62.3, 60.6, 55.1, 54.8, 53.7, 49.2, 42.1, 38.9, 38.5, 35.6, 35.4, 33.9, 33.7, 32.8, 31.8, 29.6, 29.4, 29.3, 29.1, 26.3, 25.3, 24.1, 22.6, 22.3, 20.9, 19.8, 17.3, 14.0, 12.4.

ESI-HRMS: m/z 921.8337 ([M-Cl]$^+$, C$_{60}$H$_{109}$O$_4$N$_2$ requires 921.8381).

HPLC purity >98%

Example 7

Synthesis of N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-methyl-N-octadecyloctadecan-1-aminium chloride 6g Step d) Synthesis of Compound 5g Compound 4a (0.30 g, 0.72 mmol) was dissolved in 10 ml of dry dichloromethane (DCM) and stirred for 15 min at 0° C. To the above reaction mixture, 1-Ethyl-3-(3-dimethylaminopropyl) carbodiimide (EDCI) (0.136 g, 0.72 mmol, 1 equiv) and Hydroxybenzotriazole (HOBT) (0.110 g, 0.72 mmol, 1 equiv) was added, and stirring was continued for another 30 min to activate the acid group. In a separate flask N$^1$,N$^1$-dioctadecylethane-1,2-diamine (0.527 g, 0.93 mmol, 1.3 equiv) was dissolved in 2 mL dry DCM followed by addition of di-isopropylethylamine (DIPEA) until the reaction mixture became slightly basic. Then the resulting solution was added to the above activated acid solution and the reaction was continued for 6 h. Then the reaction mixture was poured into 30 ml of DCM, washed with 1N HCl (3×20 ml), saturated NaHCO$_3$ solution (3×20 ml) and brine (3×20 ml), dried with anhydrous Na$_2$SO$_4$ and the organic layer concentrated. Then the crude was purified by column chromatography using 60-120 mesh silica gel and the compound was eluted using methanol-chloroform eluent (0.25%-0.5%, v/v) yielded compound 5g as a yellow gummy product. (0.437 g, 63% yield, $R_f$=0.70 in 5% methanol-chloroform, v/v).

$^1$H NMR (300 MHz, CDCl$_3$): δ 5.72 (s, 3H, C$_{19}$H), 4.85-4.72 (m, 1H, C$_{20}$H), 3.03-2.8 (m, 4H), 2.61-2.52 (m, 4H), 2.43-0.92 (m, 88H), 1.17 (s, 3H, C$_{19}$H), 1.14 (d, J=6.0 Hz, 3H, C$_{21}$H), 0.88 [t, J=6.3 Hz, 6H, —N(—CH$_2$—CH$_2$—(CH$_2$)$_3$—CH$_3$)$_2$], 0.66 (s, 3H, C$_{18}$H).

ESI-MS: m/z 964 ([M+H]$^+$, C$_{63}$H$_{115}$O$_4$N$_2$ requires 864.6).

Step e) f) Synthesis of Compound 6g

Compound 5g (0.130 g, 0.13 mmol) was reacted with excess methyl iodide (5 mL) and stirred for 24 h at room temperature. After that the reaction mixture was filtered, concentrated and the residue was purified by column chromatographic purification (using 100 to 200 mesh size silica gel and 1.0-1.2% methanol in chloroform was used as eluent) to give gummy solid compound which was then passed through chloride ion exchange chromatography (using Amberlite IRA-400Cl resin and methanol as eluent) yielded compound 6g as a yellowish gummy solid. (0.07 g, 55% yield, $R_f$=0.25 in 10% methanol-chloroform, v/v).

$^1$H NMR (300 MHz, CDCl$_3$): δ 8.72 (bs, 1H, —N—H), 5.72 (s, 3H, C$_{19}$H), 4.84-4.77 (m, 1H, C$_{20}$H), 3.77-3.60 (m, 4H), 3.33-3.28 (m, 4H), 3.18 (s, 3H, —OC—HN—CH$_2$—CH$_2$—N—CH$_3$), 2.57- 0.93 (m, 88H), 1.18 (s, 3H, C$_{19}$H), 1.13 (d, J=6.0 Hz, 3H, C$_{21}$H), 0.88 [t, J=6.8 Hz, 6H, —N(—CH$_2$—CH$_2$—(CH$_2$)$_3$—CH$_3$)$_2$], 0.66 (s, 3H, C$_{18}$H).

ESI-HRMS: m/z 977.8961 ([M-Cl]$^+$, C$_{64}$H$_{117}$O$_4$N$_2$ requires 977.9007).

Example 8

Cytotoxicity Studies:

Cytotoxicity assay of the different compounds were carried out by using 3-(4,5-dimethylthiazol-2-yl)-2,5-diphenyltetrazolium bromide (MTT). For this assay, 12-18 h before treatment cells were plated in 96-well plate at 5000 cells/well density. After incubation cells were treated continuously for 48 h with respective compounds at different concentration (2.5 μM-40 μM). After completion of the treatment, 10 μL of MTT solution (5 mg/mL) was added in each well and incubated for 4 h. Then the media was removed carefully, and the reduced MTT was dissolved in 1:1 (v/v) DMSO/Methanol and absorbance was measured using multimode reader (Synergy H1, BioTek). Results were represented as percentage of viability={[A550(treated cells)–background]/[A550(untreated cells)–background]}× 100. The result was summarized and provided as IC50 table in Table 1.

For combination treatment effect, cells were plated in 96 well plates at 5000 cells/well. After 18 h incubation cells were either kept untreated or treated with progesterone (compound 1, 10 μM), 10C (ten carbon long cationic chain, 10 μM), 1+10C (10 μM+10 μM) and compound 6c (10 μM) for 48 h. Following 48 h of treatment cell viability was measured following above mentioned MTT study. The results of this study are provided in FIGS. 1A-B.

The toxicity results showed that among all these derivatives 6b, 6c and 6d compounds were able to exhibit significant amount of cell killing in all tested cancer cells while remaining largely non-toxic towards tested non-cancer cells. The compiled cytotoxicity data of all the tested compounds are presented as Table 1 where IC50 of each derivative is mentioned. From this Table 1 it is clearly evident that 6c possess the highest anti-cancer activity with IC50 value recorded as 4.32±0.57, 7.33±0.19, 4.48±0.23, and 6.67±0.27 and 3.63±0.16 μM for T47D, MCF-7, OVCAR-3, MDA-MB-231 and B16F10 cells respectively.

FIGS. 1A-B show that compound 1 (progesterone), compound 10C and even their combination treatment (1+10C) did not impart any significant toxicity in all the tested cells (both cancer and non-cancer cells) at 10 μM. However, covalent conjugation of progesterone with ten-carbon long cationic chain (i.e., 6c) leads to significant toxicity only in cancer cells but not in non-cancerous cell. This result signify that toxicity shown by compound 6c resulted from covalent conjugation between progesterone with ten carbon long cationic chain and not due to ten carbon long cationic chain.

Example 9

Cell Cycle Assay:

To measure the cellular DNA content, cell cycle assay was carried out. In this assay, first cells were synchronized at early S-phase by double thymidine blocking. When cell confluency was reached around 25-30% in 60 mm dish, cells were treated with 2 mM thymidine, diluted in 10% FBS containing DMEM, for 18 h to block cells at early S-phase. To release the blocking, media was discarded and washed with 1×PBS. Then the cells were incubated with fresh cell culture media containing 10% FBS for 9 h. After releasing, second blocking was done with 2 mM thymidine containing media for 17 h. After second blocking cells were released by discarding the thymidine supplemented media and kept in fresh media. All the respective treatments for cell cycle study were done after 2 h of second release.

S-phase synchronized cells were either kept untreated or treated with compound 1 (10 μM) and 6c (10 μM) for 24 h. Cells from different treatment groups were harvested, washed with 1×PBS, and fixed with 70% ethanol and kept

TABLE 1

| Compound name | T47D | MCF7 | OVCAR-3 | B16F10 | MDA-MB-231 | NIH-3T3 | CHO | COS-1 |
| --- | --- | --- | --- | --- | --- | --- | --- | --- |
| 1 | >20 | >20 | >20 | >20 | >20 | >20 | >20 | >20 |
| 6a | 7.43 ± 0.76 | >15 | 13.92 ± 0.53 | >15 | 5.78 ± 0.38 | >20 | 17.88 ± 0.56 | >20 |
| 6b | 4.07 ± 0.23 | 8.28 ± 0.12 | 11.93 ± 0.45 | 9.95 ± 0.32 | 8.56 ± 0.52 | >20 | 16.97 ± 0.41 | >20 |
| 6c | 4.32 ± 0.57 | 7.33 ± 0.19 | 4.48 ± 0.23 | 6.67 ± 0.27 | 3.63 ± 0.16 | >20 | 17.32 ± 0.29 | >20 |
| 6d | 12.83 ± 0.43 | 7.04 ± 0.28 | 6.83 ± 0.13 | 9.54 ± 0.18 | 6.36 ± 0.19 | >20 | 17.46 ± 0.18 | >20 |
| 6e | >15 | >15 | >15 | >15 | >15 | >20 | >15 | >20 |
| 6f | >15 | >15 | >15 | >15 | >15 | >20 | >15 | >20 |
| 6g | >15 | >15 | >15 | >15 | >15 | >20 | >15 | >20 | at −20° C. for overnight. Then the ethanol was removed and washed with 1×PBS. The cells were then suspended in 500 µL of PI staining solution (50 µg/ml Propidium iodide, 0.1 mg/ml RNAse, 0.05% Triton X-100) and incubate in dark for 40 min at 37° C. After incubation cells were collected by centrifugation, washed with 1×PBS, re-suspended in 500 µL 1×PBS, and data was recorded using flow cytometer (FACS Canto II, Becton-Dickinson, San Jose, Calif., USA) and data were analyzed with FACS Diva software. A minimum of 10,000 events were gated per sample. The result of this study is provided in FIGS. 2A and 2B.

FIG. 2A reveals that 6c treated cells exhibited significantly higher amount of G2/M population while comparing with the progesterone (compound 1) treated cells. T47D (PgR-positive), B16F10 (PgR-negative), MDA-MB-231 (PgR-negative) cells were experienced 38%, 33%, 34% of the total cell population were in G2/M phase respectively following 6c treatment, while progesterone treatment showed G2/M phase population as 10%, 19%, 21% respectively. The higher amount G2/M indicates that cells are predominantly arrested in G2/M phase and hence compound 6c treatment is not allowing the cells to divide and proliferate. Thus G2/M arrest leads to the activation of cell apoptosis and then cell death.

Example 10

Quantification of Apoptosis Studies by Flow Cytometry:

Apoptosis study was performed by flow cytometry using annexin V-FITC-labeled apoptosis detection kit (Sigma) following manufacturer's protocol. Cells (□×□□□ cells/well) were seeded in six-well plates and incubate for 16-18 h. After 16-18 h, cells were either kept untreated or treated with 10 µM compound 1 and 10 µM 6c for 36 h. Next, cells were trypsinized and washed with PBS. Then the cells were re-suspended in 1× binding buffer at a density of $1\times10^6$ cells/ml and stained simultaneously with FITC-labeled annexin V (25 ng/ml) and propidium iodide (50 ng/ml). After 15 min incubation, cells were analyzed using a flow cytometer (FACS Canto II, Becton-Dickinson, San Jose, Calif., USA), and data were analyzed with FCS Express V3 software. Minimum of 10000 events were gated per sample. A result of the apoptosis study is provided in FIG. 3.

Compound 6c treated group induced significantly high amount of apoptosis (right upper and lower quadrants) in cancer cells compare to the compound 1 treated group. This effect was observed both in PgR-positive (T47D, 73% apoptotic cell) and PgR-negative (B16F10, 53.22% apoptotic cell) cells. High percentage of apoptosis in cancer cells ultimately leads to cell death, which corroborates with the cell viability data (FIG. 1A). However, normal cell (CHO) largely remains unaffected by 6c. This apoptotic study reveals that 6c treatment induces apoptosis selectively in cancer cells.

Example 11

Western Blot Study:

For in vitro cell lysate preparation, B16F10 cells were either treated with compound 1 (10 µM), 6c (10 µM) or kept untreated for 36 h continuously. After that cells were washed with cold PBS for two times, and lysed by incubating for 30 min on ice with ice-cold RIPA lysis buffer (50 mM Tris [pH 7.5], 1% NP-40, 150 mM NaCl, 0.1% sodium dodecyl sulfate [SDS], 0.5% sodium deoxycholate) containing 1% proteinase inhibitor cocktails (PIC) (Cell Signaling Technology). Following 30 min of incubation cells were centrifuged at 14,000 rpm at 4° C. for 15 minutes, supernatant was collected, and Protein concentration was measured by using BCA assay a kit (thermo scientific). For in vivo whole cell lysate, after completion of the in vivo experiment one C57BL/6J mice with representative tumor size from each group was sacrificed and tumor was collected, lysed by ice-cold RIPA buffer with 1% PIC, whole cell lysate was prepared following the same steps as mentioned above. Respective cell lysates were run in SDS-PAGE gel (8%-15%) and then the bands were transferred to polyvinylidene fluoride (PVDF) membrane. Membranes were then first incubated with respective primary antibodies and then with alkaline phosphates conjugated secondary antibody (Goat-anti-rabbit and Goat-anti-mouse). Immunodetection was performed with BCIP/NBT substrate (Sigma-Aldrich).

Antibodies Used:

Cytochrome-C (4272S), BAX (2772S), Bcl-2 (2876S), Cassepase-3 (9665S), β-actin (8457S), PI3K-p110α (4249S), PI3K-p85 (4257S), AKT (272S), p-AKT (4060S), PTEN (9552S), p-mdm2 (3521S), p53 (2524S), GAPDH (5174S) were purchased from Cell Signaling Technology; Casepase-9 (PA5-16358) was purchased from Pierce; mdm2 (ab38618) was purchased from Abcam; secondary antibodies mouse anti-rabbit IgG-PE (sc-3753) was purchased from Santa Cruz Biotechnology; Goat anti-mouse IgG Alkaline Phosphatase (DC05L) and goat anti-rabbit IgG Alkaline Phosphatase (DC06L) were purchased from Calbiochem.

FIG. 4A shows that BAX/Bcl-2 ratio in case of compound 6c treated group is almost 4 fold more compare to that of untreated group. This sequentially leads to the release of elevated expression of cytochrome C, formation of active caspase 9 and increase in level of caspase 3 expressions in 6c-treated group in B16F10 cells. Taken together, the findings summarized in FIG. 4A demonstrate that several apoptotic signaling pathways get activated upon treating cancer cells with the presently disclosed cationic progesterone molecule (6c).

FIG. 4B shows that, 36 h of 6c treatment in B16F10 cells elevated the expression level of p53, which we believe ultimately led to cell death. Towards confirming the mechanism behind this elevated p53 level, we checked how 6c treatment affected the above-mentioned pathway in B16F10. FIG. 4B clearly shows that 6c treatment led to the decrease in the expression of both catalytic and regulatory subunit of PI3K protein, which resulted in significant reduction of p-AKT level as compare to PR treated group. This reduction of p-AKT was also supported by the elevated expression of tumor suppressor PTEN protein which is a negative regulator of p-AKT. The reduced level of p-AKT was unable to activate Mdm2 to its p-mdm2 states, which is reflected by the reduced pMdm2 level in the 6c treated group. Therefore, the nuclear translocation of pMdm2 was possibly prevented which is a key step for the p53 degradation. This results support the fact that the elevation in p53 expression level by 6c could be due to the reduced p-AKT.

Example 12

In Vivo Tumor Study:

6-8 weeks old female C57BL6/J mice, obtained from CCMB (Hyderabad, India), were subcutaneously inoculated with $2.5\times10^5$ B16F10 cells in the lower left abdomen. Thirteen days after B16F10 cell inoculation, mice were grouped as per the treatment where each group contained 5 mice. The groups were as follows (i) untreated group, (ii) treated with progesterone (compound 1) (6 mg/Kg) and (iii) 6c (15 mg/Kg). Each compound suspended in PBS containing 10% DMSO and injected intraperitoneally to the respective mice. Five injections were given with a gap of 2 days. The tumor sizes were measured in volume (mm$^3$) and calculated using the formula (0.5ab$^2$), where 'a' represents the longest dimension and 'b' is the shortest dimension of the tumors. Experiment was terminated when the average tumor volume of the untreated group reached ~4000 mm$^3$. All animal work was done following the protocols approved by Institutional Animal Ethical Committee of CSIR-IICT, India.

(FIG. 5A), 6c induced significant inhibition in tumor growth and aggression in comparison to vehicle treated (UT) and progesterone-treated groups. On day 25 from tumor cell inoculation, tumor in UT group grew to ~4 times more size compared to 6c-treated group. To elucidate the possible reason for tumor inhibition, Western blot was performed with the tumor cell lysate. Tumor lysate from PR10-treated group showed increase in caspase 3 and significant increase in the p53 expression level (FIG. 5B). FIG. 5C exhibits the images of representative tumors were excised on day 25 from sacrificed mice from individual groups.

Example 13

Tunel Assay:

After completion of the in vivo experiment, one mouse from each group was sacrificed to check the apoptosis in tumor mass. First the tumors were frozen in Jung tissue medium (Leica Microsystem, Germany) followed by cryo-sectioning of 10 μm thin sections using Leica CM1850 cryostat (Germany). These were then fixed into 4% formalin for 15 min. TUNEL assay was carried out using Dead-End fluorometric apoptosis detection kit (BD Biosciences) following manufacturer's protocol. The same cryosections were washed with PBS and incubated with VE-cadherin mouse monoclonal antibody at 1:200 dilutions (Santa Cruz Biotech.) for 2 h at 4° C. to stain the blood vessel, followed by one hour incubation with goat anti-mouse IgG-PE (Santa Cruz Biotech.) secondary antibody; after that tissue sections were washed and observed under Nikon TE2000E microscope at 10× magnification.

The result of TUNEL assay (FIG. 6) shows that the number apoptotic cell in compound 6c treated mice is significantly higher as compare to the untreated or PR. Additionally, the extent of apoptosis induced in the blood vessel (compare the yellow areas in the merge panel) in 6c treated tumor sections is very high which support the anti-angiogenic effect of compound 6c. The findings from this immunohistochemical staining experiments showed that the inhibition of tumor growth by 6c could be due to induction of apoptosis both in the tumor mass and its vasculature.

Example 14

Chick Embryo Angiogenesis Study:

To measure the anti-angiogenic property chick embryo angiogenesis study was carried out. For this study, fertile chicken eggs were incubated at 37° C. humidified incubator. After four day of incubation, the cells of the eggs were cautiously removed using forceps. After that, the egg yolks were carefully treated with DMSO (20 μL; 0.1% DMSO in IX PBS), compound 1 (20 μL; 5 μM), and 6c (20 μL; 5 μM) for 4 h. Images were captured at 0 and 4 h of incubation with a stereomicroscope (Leica). Different angiogenic parameters were quantified using Angioquant software.

FIG. 7A, shows that compound 6c was able to inhibit cell growth by 50% at 2.5 μM concentrations whereas at the same concentration or even at 10 μM other treatment groups (PR, 10C, PR+10C) had little to no effect. In this CEA study the vehicle control (DMSO) and compound 1-treated embryo exhibited either no effect or little increase in the vascularization network (right upper and middle panel in FIG. 7B). However, the blood vessels were either significantly damaged or new blood vessel formation was delayed (indicated by black arrow, Right lower panel in FIG. 7B), when the embryo was incubated with compound 6c. These in vitro and CEA assay results indicate that compound 6c may have greater potential in anti-angiogenic cancer therapy.

We claim:
1. A cationic progesterone compound of formula 6:

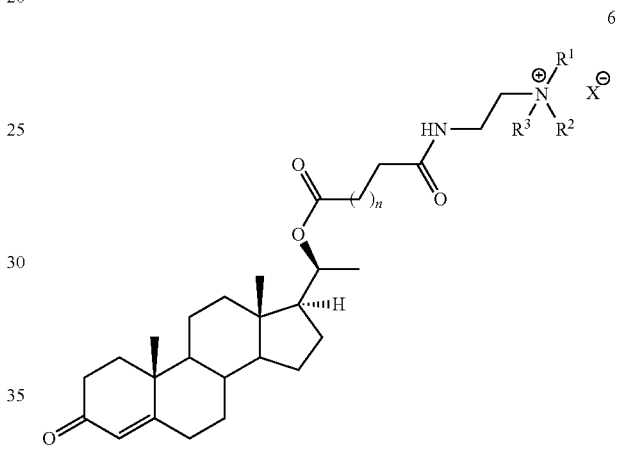

wherein: each of R$^1$ and R$^2$ is independently hydrogen or a lipophilic moiety containing a saturated alkyl chain, or a mono-, di- or tri-unsaturated alkenyl chain, each containing from 6 to 22 carbons, provided both R$^1$ and R$^2$ are not hydrogen; R$^3$ is independently a C$_1$-C$_5$ straight or branched chain alkyl group; n is an integer from 1 to 2; and X is selected from chlorine, bromine and iodine atom.

2. The compound as claimed in claim 1 wherein R$^1$ is hydrogen; and R$^2$ is a lipohilic moiety selected from the group consisting of a saturated alkyl chain and a mono-, di-, tri-unsaturated alkenyl chain, each containing from 6 to 22 carbons and vice versa.

3. The compound as claimed in claim 1, wherein the representative compounds of formula 6:
  N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobu-tanamido)ethyl)-N-hexyl-N-methylhexan-1-aminium chloride (6a)
  N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobu-tanamido)ethyl)-N-methyl-N-octyloctan-1-aminium chloride (6b)
  N-decyl-N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-methyldecan-1-aminium chloride (6c)

N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-dodecyl-N-methyldodecan-1-aminium chloride (6d)

N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-methyl-N-tetradecyltetradecan-1-aminium chloride (6e)

N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-hexadecyl-N-methylhexadecan-1-aminium chloride (6f)

N-(2-(4-((1S)-1-((10R,13S,17S)-10,13-dimethyl-3-oxo-2,3,6,7,8,9,10,11,12,13,14,15,16,17-tetradecahydro-1H-cyclopenta[a]phenanthren-17-yl)ethoxy)-4-oxobutanamido)ethyl)-N-methyl-N-octadecyloctadecan-1-aminium chloride (6g).

4. The compound as claimed in claim 1, wherein the compounds are useful as anticancer agent.

5. A process for the synthesis of a cationic progesterone compound of formula 6,

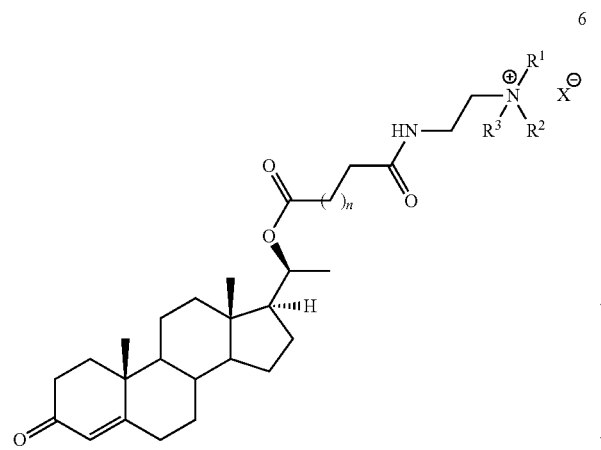

wherein: each of $R^1$ and $R^2$ is independently hydrogen or a lipophilic moiety containing a saturated alkyl chain, or a mono-, di- or tri-unsaturated alkenyl chain, each containing from 6 to 22 carbons, provided both $R^1$ and $R^2$ are not hydrogen; $R^3$ is independently a $C_1$-$C_5$ straight or branched chain alkyl group; n is an integer from 1 to 2; and X is selected from chlorine, bromine and iodine atom, wherein the process comprising steps of:

(a) reducing progesterone with lithium aluminium hydride followed by regioselective oxidation by Manganese dioxide to obtain diastereoselective secondary alcohol intermediate with general formula 3;

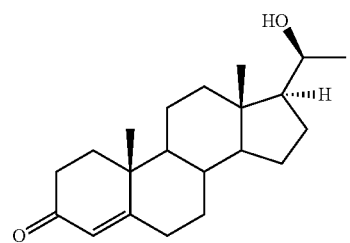

(b) introducing spacer (n=1 to 2) using cyclic anhydride followed by coupling with $N^1,N^1$-di- or mono-alkylethane-1,2-diamine in the presence of coupling agent EDCI in a solvent to obtain tertiary amine intermediate compound of general formula 5;

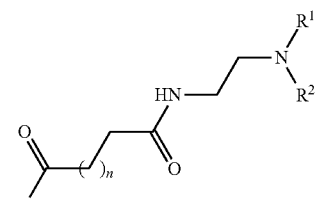

(c) reacting tertiary amine compound obtained in step (b) using alkyl halide in organic solvent followed by ion exchange chromatography using halide ion exchange resins to obtain the desired quaternized compound with general formula 6.

6. The process as claimed in claim 5, wherein the cyclic anhydride used is selected from a group consisting of succinic and glutaric anhydride.

7. The process as claimed in claim 5, wherein the $N^1,N^1$-di- or mono-alkylethane-1,2-diamine used is selected from a group consisting of saturated C2-C22 alkyl groups and/or unsaturated C2-C22 alkenyl groups containing 1, 2, or 3 double bonds.

8. The process as claimed in claim 5, wherein the solvent used is selected from a group consisting of DCM, dimethyl formamide and 1,4 dioxane.

9. A pharmaceutical composition for the treatment of cancer comprising an effective amount of the compound of formula as claimed in claim 1 individually or in combination thereof, optionally, along with the pharmaceutically acceptable excipients, diluents.

* * * * *